(12) United States Patent
Mascia

(10) Patent No.: US 7,476,777 B2
(45) Date of Patent: Jan. 13, 2009

(54) BIOLOGICAL CONTAINMENT SYSTEM

(75) Inventor: Peter N. Mascia, Thousand Oaks, CA (US)

(73) Assignee: Ceres, Inc., Thousand Oaks, CA (US)

( * ) Notice: Subject to any disclaimer, the term of this patent is extended or adjusted under 35 U.S.C. 154(b) by 480 days.

(21) Appl. No.: 10/873,679

(22) Filed: Jun. 22, 2004

(65) Prior Publication Data

US 2007/0039066 A1    Feb. 15, 2007

Related U.S. Application Data

(63) Continuation-in-part of application No. 10/667,295, filed on Sep. 17, 2003, now abandoned.

(60) Provisional application No. 60/411,823, filed on Sep. 17, 2002.

(51) Int. Cl.
*C12N 15/82* (2006.01)
*A01H 5/00* (2006.01)
*A01H 5/10* (2006.01)
*C12P 21/00* (2006.01)

(52) U.S. Cl. ............... 800/278; 800/288; 800/300; 435/69.1

(58) Field of Classification Search ............ None
See application file for complete search history.

(56) References Cited

U.S. PATENT DOCUMENTS

| | | |
|---|---|---|
| 4,654,465 A | 3/1987 | Brar et al. |
| 4,727,219 A | 2/1988 | Brar et al. |
| 4,761,373 A | 8/1988 | Anderson et al. |
| 4,769,061 A | 9/1988 | Comai |
| 4,810,648 A | 3/1989 | Stalker |
| 4,936,904 A | 6/1990 | Carlson |
| 4,940,835 A | 7/1990 | Shah et al. |
| 4,946,778 A | 8/1990 | Ladner et al. |
| 4,975,374 A | 12/1990 | Goodman et al. |
| 5,004,864 A | 4/1991 | Robertson et al. |
| 5,013,659 A | 5/1991 | Bedbrook et al. |
| 5,034,323 A | 7/1991 | Jorgensen et al. |
| 5,162,602 A | 11/1992 | Somers et al. |
| 5,204,253 A | 4/1993 | Sanford et al. |
| 5,276,268 A | 1/1994 | Strauch et al. |
| 5,432,068 A | 7/1995 | Albertsen et al. |
| 5,538,880 A | 7/1996 | Lundquist et al. |
| 5,554,798 A | 9/1996 | Lundquist et al. |
| 5,561,236 A | 10/1996 | Leemans et al. |
| 5,591,616 A | 1/1997 | Hiei et al. |
| 5,704,160 A | 1/1998 | Bergquist et al. |
| 5,706,603 A | 1/1998 | Bergquist et al. |
| 5,723,765 A | 3/1998 | Oliver et al. |
| 5,767,366 A | 6/1998 | Sathasivan et al. |
| 5,773,697 A | 6/1998 | Tomes et al. |
| 5,824,779 A | 10/1998 | Koegel et al. |
| 5,824,798 A | 10/1998 | Tallberg et al. |
| 5,879,903 A | 3/1999 | Strauch et al. |
| 5,880,333 A | 3/1999 | Goff et al. |
| 5,900,525 A | 5/1999 | Austin-Phillips et al. |
| 5,907,082 A | 5/1999 | O'Neill et al. |
| 5,922,934 A | 7/1999 | Bergquist et al. |
| 5,928,937 A | 7/1999 | Kakefuda et al. |
| 5,958,745 A | 9/1999 | Gruys et al. |
| 6,013,863 A | 1/2000 | Lundquist et al. |
| 6,063,985 A | 5/2000 | Chua et al. |
| 6,084,155 A | 7/2000 | Volrath et al. |
| 6,087,558 A | 7/2000 | Howard et al. |
| 6,093,874 A | 7/2000 | Jofuku et al. |
| 6,127,606 A | 10/2000 | Bennett et al. |
| 6,136,320 A | 10/2000 | Arntzen et al. |
| 6,147,282 A | 11/2000 | Goff et al. |
| 6,229,064 B1 | 5/2001 | Fischer et al. |
| 6,232,526 B1 | 5/2001 | McElroy et al. |
| 6,235,974 B1 | 5/2001 | Qiu et al. |
| 6,235,975 B1 | 5/2001 | Harada et al. |
| 6,248,940 B1 | 6/2001 | Berquist |
| 6,255,562 B1 | 7/2001 | Heyer et al. |
| 6,255,564 B1 | 7/2001 | Fabijanski et al. |
| 6,262,334 B1 | 7/2001 | Endege et al. |
| 6,262,341 B1 | 7/2001 | Baszczynski et al. |
| 6,271,016 B1 | 8/2001 | Anderson et al. |
| 6,303,341 B1 | 10/2001 | Hiatt et al. |

(Continued)

FOREIGN PATENT DOCUMENTS

EP        0 242 246        10/1987

(Continued)

OTHER PUBLICATIONS

Sessa et al. Plant Molecular Biology 29: 969-982 (1995).*

(Continued)

*Primary Examiner*—David T Fox
(74) *Attorney, Agent, or Firm*—Fish & Richardson P.C.

(57) ABSTRACT

The invention relates to materials and methods useful for controlling the unwanted spread of transgenic traits. The methods involve an apomictic plant containing a transgene for a desired trait and a transgene causing seed infertility. The methods also involve one or more transcription activators that activates expression of both transgenes carried by the apomictic plant. The transcription activator(s) activates expression of both transgenes in the female. Seeds that are formed on such plants are infertile.

14 Claims, No Drawings

U.S. PATENT DOCUMENTS

| | | | |
|---|---|---|---|
| 6,320,102 | B1 | 11/2001 | Harada et al. |
| 6,326,527 | B1 | 12/2001 | Kirihara et al. |
| 6,329,571 | B1 | 12/2001 | Hiei |
| 6,362,394 | B1 | 3/2002 | Crossland et al. |
| 6,392,119 | B1 | 5/2002 | Gutterson et al. |
| 6,399,856 | B1 | 6/2002 | Cigan et al. |
| 6,417,429 | B1 | 7/2002 | Hein et al. |
| 6,451,732 | B1 | 9/2002 | Beckett et al. |
| 6,451,735 | B1 | 9/2002 | Ottaway et al. |
| 6,492,577 | B1 | 12/2002 | Harada et al. |
| 6,541,610 | B1 | 4/2003 | Smith |
| 6,559,357 | B1 | 5/2003 | Fischer et al. |
| 6,781,035 | B1 | 8/2004 | Harada et al. |
| 6,815,577 | B1 | 11/2004 | Harper et al. |
| 6,825,397 | B1 * | 11/2004 | Lowe et al. .................. 800/278 |
| 6,906,244 | B2 | 6/2005 | Fischer et al. |
| 6,946,586 | B1 | 9/2005 | Fromm et al. ............... 800/278 |
| 2001/0016956 | A1 | 8/2001 | Ward et al. |
| 2002/0081667 | A1 | 6/2002 | Gorlach et al. |

FOREIGN PATENT DOCUMENTS

| | | |
|---|---|---|
| EP | 329308 | 2/1989 |
| EP | 0 823 480 | 2/1998 |
| EP | 1 461 438 | 9/2004 |
| WO | 90/08828 | 8/1990 |
| WO | 97/31064 | 8/1997 |
| WO | 98/08961 | 3/1998 |
| WO | 98/28431 | 7/1998 |
| WO | 98/36083 | 8/1998 |
| WO | 98/36090 | 8/1998 |
| WO | 98/53083 | 11/1998 |
| WO | 99/32619 | 7/1999 |
| WO | 99/53050 | 10/1999 |
| WO | 99/67405 | 12/1999 |
| WO | 00/24914 | 5/2000 |
| WO | 00/28058 | 5/2000 |
| WO | 00/37660 | 6/2000 |
| WO | 00/40694 | 7/2000 |
| WO | 2004/027038 | 4/2004 |
| WO | WO2004/027038 | 4/2004 |

OTHER PUBLICATIONS

Kandasamy et al. The Plant Cell 5(3): 263-275 (Mar. 1993).*
GenBank Accession No. ACC39488.
GenBank Accession No. J02798.
GenBank Accession No. J05212.
GenBank Accession No. L05934.
GenBank Accession No. M63985.
GenBank Accession No. U09118.
GenBank Accession No. U09119.
GenBank Accession No. U39944.
GenBank Accession No. U93215.
GenBank Accession No. Z17657.
Abler and Scandalios, "Isolation and characterization of a genome sequence encoding the maize Cat3 catalase gene," *Plant Mol. Biol.*, 1993, 22:1031-1038.
Aoyama and Chua, "A glucocorticoid-mediated transcriptional induction system in transgenic plants," *Plant Journal*, 1997, 11(3):605-612.
Austin et al., "An Overview of a Feasibility Study for the Production of Industrial Enzymes in Transgenic Alfalfa," *Annals NY Acad. Sci.*, 1994, 721:234-244.
Austin et al., "Production and field performance of transgenic alfalfa (*Medicago sativa* L.) expressing alpha-amylase and manganese-dependent lignin peroxidase," *Euphytica*, 1995, 85:381-393.
Bai et al., "Isolation and Characterization of *SYN1*, a *RAD21*-like Gene Essential for Meiosis in *Arabidopsis*," *Plant Cell*, 1999, 11:417-430.

Blume and Grierson, "Expression of ACC oxidase promoter—GUS fusions in tomato and *Nicotiana plumbaginifolia* regulated by developmental and environmental stimuli," *Plant J.*, 1997, 12:731-746.
Bossinger and Smyth, "Initiation patterns of flower and floral organ development in *Arabidopsis thaliana*," *Development*, 1996, 122:1093-1102.
Bowman, "Expression of the *Arabidopsis* Floral Homeotic Gene Agamous Is Restricted to Specific Cell Types Late in Flower Development," *Plant Cell*, 1991, 3:749-758.
Bustos et al., "Regulation of β-Glucuronidase Expression in Transgenic Tobacco Plants by an A/T-Rich, cis-Acting Sequence Found Upstream of a French Bean β-Phaseolin Gene," *Plant Cell*, 1989, 1:839-853.
Caddick et al., "An ethanol inducible gene switch for plants used to manipulate carbon metabolism," *Nat. Biotechnology*, 1998, 16(2):177-180.
Chen and Foolad, "Molecular organization of a gene in barley which encodes a protein similar to aspartic protease and its specific expression in nucellar cells during degeneration," *Plant Mol. Biol.*, 1997, 35:821-831.
Choi et al., "Tissue-specific and developmental regulation of a gene encoding a low molecular weight sulfur-rich protein in soybean seeds," *Mol. Gen. Genet.*, 1995, 246:266-268.
Colombo et al., "Downregulation of Ovule-Specific MADS Box Genes from Petunia Results in Maternally Controlled Defects in Seed Development," *Plant Cell*, 1997, 9:703-715.
Conceição and Krebbers, "A cotyledon regulatory region is responsible for the different spatial expression patterns of *Arabidopsis* 2S albumin genes," *Plant J.*, 1994, 5(4):493-505.
Dasgupta et al., "Cloning and sequencing of 5' flanking sequence from the gene encoding 2S storage protein, from two *Brassica* species,", *Gene*, 1993, 133:301-302.
Dieffenbach and Dveksler (eds.), *PCR Primer: A Laboratory Manual*, 1995, Cold Spring Harbor Laboratory Press (TOC only).
Drews et al., "Negative Regulation of the *Arabidopsis* Homeotic Gene AGAMOUS by the APETALA2 Product," *Cell*, 1991, 65:991-1002.
Ficker et al., "A promoter directing high level expression in pistils of transgenic plants," *Plant Mol. Biol.*, 1997, 35:425-431.
Ficker et al., "Multiple elements of the S2-RNase promoter from potato (*Solanum tuberosum* L.) are required for cell type-specific expression in transgenic potato and tobacco," *Mol. Gen. Genet.*, 1998, 257:132-142.
Gatz, "Chemical Control of Gene expression," *Annual Review of Plant Physiology and Plant Molecular Biology*, 1997, 48:89-108.
Green et al., "Binding site requirements for pea nuclear protein factor GT-1 correlate with sequences required for light-dependent transcriptional activation of the rbcS-3A gene," *EMBO J.*, 1988, 7(13):4035-4044.
Guerrero et al., "Promoter sequences from a maize pollen-specific gene direct tissue-specific transcription in tobacco," *Mol. Gen. Genet.*, 1990, 224(1):161-168.
Gustafson-Brown et al., "Regulation of the *Arabidopsis* Floral Homeotic Gene APETALA1," *Cell*, 1994, 76(1):131-143.
Ji and Langridge, "An early meiosis cDNA clone from wheat," *Mol. Gen. Genet.*, 1994, 243(1):17-23.
Jordano et al., "A Sunflower Helianthinin Gene Upstream Sequence Ensemble Contains an Enhancer and Sites of Nuclear Protein Interaction," *Plant Cell*, 1989, 1:855-866.
Josefsson et al., "Structure of a Gene Encoding the 1.7 S Storage Protein, Napin, from *Brassica napus*," *J. Biol. Chem.*, 1987, 262:12196-12201.
Klimyuk and Jones, "AtDMC1, the *Arabidopsis* homologue of the yeast DMC1 gene: characterization, transposon-induced allelic variation and meiosis-associated expression," *Plant J.*, 1997, 11(1):1-14.
Kobayashi et al., "Characterization of cDNAs Induced in Meiotic Prophase in Lily Microsporocytes," *DNA Res.*, 1994, 1:15-26.
Kulikauskas and McCormick, "Identification of the tobacco and *Arabidopsis* homologues of the pollen-expressed LAT59 gene tomato," *Plant Mol. Biol.*, 1997, 34:809-814.
Lee and Huang, "Genes encoding oleosins in maize kernel of inbreds Mo17 and B73," *Plant Mol. Biol.*, 1994, 26(6):1981-1987.

Mandel et al., "Molecular characterization of the *Arabidopsis* floral homeotic gene APETALA1," *Nature*, 1992, 360:273-277.

Meier et al., "Elicitor-Inducible and Constitutive in Vivo DNA Footprints Indicate Novel cis-Acting Elements in the Promoter of a Parsley Gene Encoding Pathogenesis-Related Protein 1," *Plant Cell*, 1991, 3:309-315.

Owen and Pen (eds.), "Transgenic Plants: A Production System for Industrial and Pharmaceutical Proteins," John Wiley & Son Ltd.; Austin, S. et al., 1994. *Annals NY Acad.Sci.*, 1996, 721:234-242.

Ray et al., "*Arabidopsis* floral homeotic gene BELL (BEL1) controls ovule development through negative regulation of AGAMOUS gene (AG)," *Proc. Natl. Acad. Sci. USA*, 1994, 91:5761-5765.

Reiser et al., "The BELL1 Gene Encodes a Homeodomain Protein Involved in Pattern Formation in the *Arabidopsis* Ovule Primordium," *Cell*, 1995, 83:735-742.

Rotino et al., "Genetic engineering of parthenocarpic plants," *Nat. Biotechnol.*, 1997, 15:1398-1401.

Sambrook et al., Molecular Cloning: A Laboratory Manual, 1989, 2nd edition, *Cold Spring Harbor Press*, Plainview, NY, Sections 9.37-9.52.

Schernthaner et al., "Control of seed germination in transgenic plants based on the segregation of a two-component genetic system," *Proc. Natl. Acad. Sci. USA*, 2003, 100:6855-6859.

Sheridan et al., "The mac1 Gene: Controlling the Commitment to the Meiotic Pathway in Maize," *Genetics*, 1996, 142:1009-1020.

Sjödahl et al., "Deletion analysis of the *Brassica napus* cruciferin gene *cru 1* promoter in transformed tobacco: promoter activity during early and late stages of embryogenesis is influenced by *cis*-acting elements in partially separate regions," *Planta*, 1995, 197(2):264-271.

Treacy et al., "Bnm1, a *Brassica* pollen-specific gene," *Plant Mol. Biol.*, 1997, 34:603-611.

Urao et al., "Molecular cloning and characterization of a gene that encodes a MYC-related protein in *Arabidopsis*," *Plant Mol. Biol.*, 1996, 32(3):571-576.

Wakeley et al., "A maize pectin methylesterase-like gene, ZmC5, specifically expressed in pollen," *Plant Mol. Biol.*, 1998, 37:187-192.

Yadegari et al., "Mutations in the FIE and MEA Genes That Encode Interacting Polycomb Proteins Cause Parent-of-Origin Effects on Seed Development by Distinct Mechanisms," *Plant Cell*, 2000, 12:2367-2382.

Zhang et al., "DNA Sequences That Activate Isocitrate Lyase Gene Expression during Late Embryogenesis and during Postgerminative Growth," *Plant Physiology*, 1996, 110:1069-1079.

Ziegelhoffer et al., "Dramatic effects of truncation and sub-cellular targeting on the accumulation of recombinant microbial cellulase in tobacco," *Molecular Breeding*, 2001, 8:147-158.

Ziegelhoffer et al., "Expression of bacterial cellulase genes in transgenic alfalfa (*Medicago sativa* L.), potato (*Solanum tuberosum* L.) and tobacco (*Nicotiana tabacum* L.)," *Molecular Breeding*, 1999, 5:309-318.

Schena et al. "A steroid-inducible gene expression system for plant cells" *Proc. Natl. Acad. Sci. USA*, Dec. 1991, 88:10421-10425.

Lloyd et al. "Epidermal Cell Fate Determination in *Arabidopsis*: Patterns Defined by a Steroid-Inducible Regulator" *Science*, Oct. 21, 1994, 266(5184):436-439.

Bruce et al., "Expression Profiling of the Maize Flavonoid Pathway Genes Controlled by Estradiol-Inducible Transcription Factors CRC and P" *The Plant Cell*, 2000, 12:65-79.

Daniell, "Molecular strategies for gene containment in transgenic crops" *Nature Biotechnology*, 2002, 20(6):581-586.

de Pater et al. Characterization of a zinc-dependent transcriptional activator from *Arabidopsis*, 1996, 24(23):4624-4631.

Escriva et al. "Ligand binding and nuclear receptor evolution" *BioEssays*, 2000, 22:717-727.

Guyer et al. "Activation of Latent Transgenes in Arabidopsis Using a Hybrid Transcription Factor" *Genetics*, 1998, 149:633-639.

Mascia et al. "Safe and acceptable strategies for producing foreign molecules in plants" *Current Opinion in Plant Biology*, 2004, 7:189-195.

Meshi et al. "Plant Transcription Factors" *Plant Cell Physiology*, 1995, 36(8):1405-1420.

Olefsky "Nuclear Receptor Minireview Series" *The Journal of Biological Chemistry*, 2001, 276(4):36863-36864.

Riechmann et al. "A genomic perspective on plant transcription factors" *Current Opinion in Plant Biology*, 2000, 3:423-434.

Riechmann et al. "*Arabidopsis* Transcription Factors: Genome-Wide Comparative Analysis Among Eukaryotes" *Science*, 2000, 290:2105-2110.

Struhl "Helix-turn-helix, zinc finger, and leucin-zipper motifs for eukaryotic transcriptional regulatory proteins" *TIBS*, 1989, 137-140.

Batard et al. "Increasing expression of P450 and P450-reductase proteins from monocots in heterologous systems" *Arch. Biochem. Biophys.* 379:161-169 (2000).

Campbell and Gowri "Codon usage in higher plants, green algae, and cyanobacteria" *Plant Physiology*, 92:1-11(1990).

Place database release 11.0, obtained from the Internet at http://ftp.dna.affrc.go.jp/pub/dna_place/r11.0/place.seq, document dated Sep. 10, 2002, 181 pages.

Rouwendal et al. "Enhanced expression in tobacco of the gene encoding green fluorescent protein by modification of its codon usage" *Plant Mol. Biol.*, 33:989-999 (1997).

Streatfield et al. "Plant-based vaccines: unique advantages" *Vaccine*, 19:2742-2748 (2001).

Streatfield "Approaches to achieve high-level heterologous protein production in plants" *Plant Biotechnology*, 5:2-15 (2007).

* cited by examiner

BIOLOGICAL CONTAINMENT SYSTEM

CROSS REFERENCE TO RELATED APPLICATION

This application claims priority to and is a continuation-in-part of U.S. application Ser. No. 10/667,295, filed Sep. 17, 2003, now abandoned, and U.S. Provisional Application No. 60/411,823, filed Sep. 17, 2002, both of which are incorporated by reference in their entirety.

REFERENCE TO TABLE SUBMITTED ON A COMPACT DISC

This application includes a compact disc (Disc 1 of 2, submitted in duplicate) containing Tables. The entire contents of the Tables are herein incorporated by reference. The Tables are identified on the compact disc as follows.

The compact disc contains Reference Tables designated: reference_table1__4565.710-0004-55300-US-U-36440.01__1.txt; reference_table2__3847.710-0004-55300-US-U-36440.01__1.txt; reference_table3__3769.710-0004-55300-US-U-36440.01__1.txt; reference_table4__3708.710-0004-55300-US-U-36440.01__1.txt; and reference_table5__311987.710-0004-55300-US-U-36440.01__1.txt. The compact disc also contains an ortholog table designated ortholog.txt.

| File name | Size (kilobytes) | Date of Creation |
|---|---|---|
| reference_table1__311987.710-0004-55300-US-U-36440.01__1.txt | 59.9 KB | Feb. 29, 2004 |
| reference_table2__3708.710-0004-55300-US-U-36440.01__1.txt | 82.2 KB | Feb. 26, 2004 |
| reference_table3__3769.710-0004-55300-US-U-36440.01__1.txt | 99.1 KB | Feb. 26, 2004 |
| reference_table4__3847.710-0004-55300-US-U-36440.01__1.txt | 110 KB | Feb. 26, 2004 |
| reference_table5__4565.710-0004-55300-US-U-36440.01__1.txt | 44.5 KB | Feb. 26, 2004 |
| Ortholog.txt | 6.00 KB | Mar. 15, 2004 |

The compact disc also contains a Consensus Sequence Table containing consensus sequences designated: 12514_gly_bra; 12514; 12653917; 23771; 3000_dico; 3000; 1610; 519; 8916; 38419_mono; 38419; 38419_dico; 32791; 32348; 5605; 5605_gly_bra; and 519_gly.

| File Name | Size (kilobytes) | Date of Creation |
|---|---|---|
| Consensus Sequence Table.txt | 16.5 KB | May 4, 2004 |

The compact disc also contains Matrix Tables designated 12514_gly_bra_matrix_table1.txt; 12514_matrix_table2.txt; 12653917_matrix_table3.txt; 23771-matrix_table4.txt; 3000_dico_matrix_table5.txt; 3000_matrix_table6.txt; 1610_matrix_table7.txt; 519_matrix_table8.txt; 8916_matrix_table9txt; 38419_mono_matrix_table10.txt; 38419_matrix_table11.txt; 38419_dico_matrix_table12.txt; 32791_matrix_table13.txt; 32348_matrix_table14.txt; 5605_matrix_table15.txt; 5605_gly_bra_matrix_table16.txt; and 519_gly_matrix_table17.txt.

| File Name | Size (kilobytes) | Date of Creation |
|---|---|---|
| 12514_gly_bra_matrix_1.txt | 4.55 KB | Apr. 13, 2004 |
| 12514_matrix_2.txt | 5.19 KB | Apr. 13, 2004 |
| 12653917_matrix_3.txt | 48.6 KB | Apr. 21, 2004 |
| 1610_matrix_7.txt | 6.39 KB | Apr. 9, 2004 |
| 23771_matrix_4.txt | 5.07 KB | Apr. 8, 2004 |
| 3000_dico_matrix_5.txt | 11.7 KB | Apr. 23, 2004 |
| 3000_matrix_6.txt | 10.4 KB | Apr. 9, 2004 |
| 32348_matrix_14.txt | 18.4 KB | Apr. 23, 2004 |
| 32791_matrix_13.txt | 9.21 KB | Apr. 13, 2004 |
| 38419_dico_matrix_12.txt | 12.5 KB | Apr. 23, 2004 |
| 38419_matrix_11.txt | 14.1 KB | Apr. 21, 2004 |
| 38419_mono_matrix_10.txt | 12.4 KB | Apr. 14, 2004 |
| 519_gly_matrix_17.txt | 2.07 KB | Apr. 9, 2004 |
| 519_matrix_8.txt | 4.14 KB | Apr. 9, 2004 |
| 5605_gly_bra_matrix_16.txt | 3.26 KB | Apr. 22, 2004 |
| 5605_matrix_15.txt | 3.12 KB | Apr. 9, 2004 |
| 8916_matrix_9.txt | 7.70 KB | Apr. 16, 2004 |

All of the above computer files are incorporated by reference in their entirety.

REFERENCE TO SEQUENCE LISTING SUBMITTED ON A COMPACT DISC

This application includes a compact disc (Disc 2 of 2, submitted in duplicate) containing a sequence listing. The entire content of the sequence listing is herein incorporated by referenced. The sequence listing is identified on the compact disc as follows.

| File Name | Size (bytes) | Date of Creation |
|---|---|---|
| 11696-109001.TXT | 606,208 | Jun. 21, 2004 |

The invention relates to methods and materials for maintaining the integrity of the germplasm of transgenic and conventionally bred plants. In particular, the invention pertains to methods and materials that can be used to minimize the unwanted transmission of transgenic traits.

BACKGROUND

Transgenic plants are now common in the agricultural industry. Such plants express novel transgenic traits such as insect resistance, stress tolerance, improved oil quality, improved meal quality and heterologous protein production. As more and more transgenic plants are developed and introduced into the environment, it is important to control the undesired spread of transgenic traits from transgenic plants to other traditional and transgenic cultivars, plant species and breeding lines.

While physical isolation and pollen trapping border rows have been employed to control transgenic plants under study conditions, these methods are cumbersome and are not practical for many cultivated transgenic plants. Effective ways to control the transmission and expression of transgenic traits without intervention would be useful for managing transgenic plants.

One recent genetic approach involves the production of transgenic plants that comprise recombinant traits of interest linked to repressible lethal genes. See, WO 00/37660. The lethal genes are blocked by the action of repressor molecules produced by repressor genes located at a different genetic locus. The lethal phenotype is expressed only if the repressible lethal gene construct and the repressor gene segregate after meiosis. This approach reportedly can be used to maintain genetic purity by blocking introgression of genes from plants that lack the repressor gene.

SUMMARY

The present invention features methods and materials useful for controlling the transmission and expression of transgenic traits. The methods and materials of the invention facilitate the cultivation of transgenic plants without the undesired transmission of transgenic traits to other plants.

The invention features a method for making infertile seed. The method comprises permitting seed development to occur on a plurality of first plants that have been pollinated by a plurality of second plants. The first plants are male-sterile and comprise first and second nucleic acids. The first nucleic acid comprises a first transcription activator recognition site and a first promoter, operably linked to a sequence to be transcribed. The second nucleic acid comprises a second transcription activator recognition site and a second promoter, operably linked to a coding sequence causing seed infertility. The second plants are male-fertile and comprise at least one activator nucleic acid comprising at least one coding sequence for a transcription activator that is effective for binding to at least one of the above recognition sites. Each transcription activator coding sequence has a promoter operably linked thereto. The resulting seeds are infertile. The at least one activator nucleic acid can be a single nucleic acid encoding a single transcription activator that binds to both the first and second recognition sites. In some embodiments, the at least one activator nucleic acid is two nucleic acids, each encoding different transcription activators, one of which can bind the first recognition site and the other of which can bind the second recognition site. Alternatively, the at least one activator nucleic acid can be a single nucleic acid encoding a first transcription activator that can bind the first recognition site and encoding a second transcription activator that can bind the second recognition site. The promoter for the transcription activator can be seed-specific, or can be chemically inducible. The plants can be dicotyledonous plants, or monocotyledonous plants. The method can further comprise the step of harvesting the seeds. The plurality of first plants can be cytoplasmically male-sterile, or genetically male-sterile.

In some embodiments, the sequence to be transcribed encodes a preselected polypeptide, and the seeds can have a statistically significant increase in the amount of the preselected polypeptide relative to seeds that do not contain or express the first nucleic acid. The preselected polypeptide can be an antibody, or an industrial enzyme.

The sequence causing seed infertility can encode a seed infertility polypeptide, such as a loss-of-function mutant FIE polypeptide, a LEC2 polypeptide, an ANT polypeptide, or a LEC1 polypeptide.

The invention also features a method for making a polypeptide, which comprises obtaining seed produced by pollination of a male-sterile plant. Such seed comprises a first nucleic acid comprising a first recognition site for a transcription activator and a first promoter, operably linked to a sequence to be transcribed. Such seed also comprises a second nucleic acid comprising a second recognition site for a transcription activator and a second promoter, operably linked to a sequence causing seed infertility. Such seed also comprises at least one activator nucleic acid comprising at least one coding sequence for a transcription activator that binds to at least one of said recognition sites, each of the at least one transcription activators having a promoter operably linked thereto. The seeds are infertile and have a statistically significant increase in the amount of an endogenous polypeptide relative to seeds that do not contain or express said first nucleic acid. The endogenous polypeptide can be extracted from the seed.

A method for making a polypeptide can comprise permitting a plurality of first, male-sterile, plants to be pollinated by a plurality of second plants. The first plants comprise a first nucleic acid comprising a first transcription activator recognition site and a first promoter, operably linked to a coding sequence encoding a preselected polypeptide; and a second nucleic acid comprising a second transcription activator recognition site and a second promoter, operably linked to a sequence causing seed infertility. The second plants comprise at least one activator nucleic acid encoding at least one transcription activator that binds to at least one of the recognition sites. Each of the at least one transcription activators has a promoter operably linked thereto. The method also comprises harvesting seeds from the plurality of first plants. The resulting said seeds are infertile and have a statistically significant increase in the amount of preselected polypeptide relative to seeds that do not contain or express the first nucleic acid. The method can also comprise extracting the preselected polypeptide from the seeds. The plurality of first plants and said plurality of second plants can be randomly interplanted.

The invention also features an article of manufacture, which comprises a container, a first type of seeds within the container, and a second type of seeds within the container. The first type of seeds comprise at least one first nucleic acid comprising a first transcription activator recognition site and a first promoter, operably linked to a sequence to be transcribed, and a second transcription activator recognition site and a second promoter, operably linked to a sequence causing seed infertility. Plants grown from the first type of seeds are male-sterile. The second type of seeds comprise at least one activator nucleic acid, which encodes one or more transcription activators that are effective for binding to a corresponding one or more of the recognition sites, each transcription activator coding sequence has a promoter operably linked thereto. Plants grown from the second type of seeds are male-fertile. The sequence to be transcribed can encode a preselected polypeptide. The ratio of the first type of seeds to the second type of seeds can be about 70:30 or greater. The first and second types of seeds can be monocotyledonous seeds or dicotyledonous seeds. The invention also features a plant grown from one of the above types of seeds.

The invention also features a nucleic acid construct comprising a first transcription activator recognition site and a first promoter. The first recognition site and first promoter are operably linked to a sequence to be transcribed. The nucleic acid construct also comprises a second transcription activator recognition site and a second promoter, each of which are operably linked to a second coding sequence encoding a seed infertility factor. The sequence causing seed infertility can be transcribed into a FIE antagonist, e.g., a FIE antisense RNA, or a ribozyme, or a chimeric polypeptide comprising a polypeptide segment exhibiting histone acetyltransferase activity fused to a polypeptide segment exhibiting activity of a subunit of a chromatin-associated protein complex having histone deacetylase activity. The sequence to be transcribed in the nucleic acid construct can encode a preselected polypeptide, e.g., an antibody, a polypeptide that has immunogenic activity in a mammal, or an industrial enzyme such as glucose-6-phosphate dehydrogenase or alpha-amylase. The sequence causing seed infertility can encode a LEC2 polypeptide, an ANT polypeptide or a LEC1 polypeptide.

The invention also features a method for making infertile seed. A plurality of male-sterile first plants are provided for the method, each such plant comprising a first nucleic acid and a second nucleic acid. The first nucleic acid comprises a first transcription activator recognition site and a first promoter. The first recognition site and the first promoter are operably linked to a sequence to be transcribed. The second nucleic acid comprises a second transcription activator recognition site and a second promoter. The second recognition site and the second promoter are operably linked to a sequence that results in seed infertility. A plurality of male-fertile second plants are provided for the method, each such plant comprising at least one activator nucleic acid. The activator nucleic acid comprises at least one coding sequence for a transcription activator that binds to at least one of the recognition sites, and each at least one transcription activator coding sequence has a promoter operably linked to it. Seed development is permitted to occur on the first plants after pollination by pollen from the second plants. The seeds are infertile such that the seeds produce no seedlings or seedlings that are not fertile.

The invention also features a method for making infertile seed. The method comprises growing a plurality of apomictic plants that comprise first and second nucleic acids, wherein seeds that form on the plants are infertile. The first nucleic acid comprises a first transcription activator recognition site and a first promoter, the first recognition site and first promoter operably linked to a sequence to be transcribed. The second nucleic acid comprises a second transcription activator recognition site and a second promoter, the second recognition site and second promoter operably linked to a coding sequence that results in seed infertility. Such plants comprise at least one activator nucleic acid having at least one coding sequence for a transcription activator that binds to at least one of the recognition sites, each transcription activator coding sequence having a promoter operably linked thereto. The at least one activator nucleic acid can be a single nucleic acid encoding a first transcription activator that binds the first recognition site and a second transcription activator that binds the second recognition site.

The promoter for the first transcription activator can be a constitutive promoter and the promoter for the second transcription activator can be a seed-specific promoter. The promoter for the first transcription activator can be a maize ubiquitin promoter. The promoter for the first transcription activator can be a vegetative tissue-specific promoter and the promoter for the second transcription activator can be a seed-specific promoter. The apomictic plants can be dicotyledonous plants or monocotyledonous plants. The sequence to be transcribed can encode a preselected polypeptide. Expression of the preselected polypeptide can confer herbicide resistance. The sequence causing seed infertility can encode a seed infertility polypeptide. The seed infertility polypeptide can be a loss-of-function mutant FIE polypeptide, an ANT polypeptide, or a LEC1 polypeptide.

The invention also features a method for making a polypeptide. The method comprises growing a plurality of apomictic plants, each of such plants comprising a first nucleic acid and a second nucleic acid. The first nucleic acid comprises a first transcription activator recognition site and a first promoter, the first recognition site and first promoter operably linked to a nucleic acid encoding a preselected polypeptide. The second nucleic acid comprises a second transcription activator recognition site and a second promoter, the second recognition site and second promoter operably linked to a sequence causing seed infertility. Each plant also has at least one activator nucleic acid encoding at least one transcription activator that binds to at least one of the recognition sites, each transcription activator nucleic acid having a promoter operably linked thereto. The method further comprises expressing the preselected polypeptide in the plants. The plants have a statistically significant increase in the preselected polypeptide relative to plants that do not contain or express the first nucleic acid. Seeds that develop on the plants are infertile.

The invention also features an article of manufacture comprising a container, and seeds from an apomictic species within the container. The seeds comprise at least one first nucleic acid comprising a first transcription activator recognition site and a first promoter, the first recognition site and first promoter operably linked to a sequence to be transcribed. The seeds also comprise a second transcription activator recognition site and a second promoter, the second recognition site and second promoter operably linked to a sequence causing seed infertility. Plants grown from the seeds are infertile and further contain at least one activator nucleic acid encoding at least one transcription activator that binds to at least one of the recognition sites. Each transcription activator has a promoter operably linked thereto.

The sequence to be transcribed can be a preselected polypeptide. The at least one first nucleic acid can comprise a nucleic acid comprising the first transcription activator recognition site, the first promoter and the sequence to be transcribed, and a different nucleic acid comprising the second transcription activator recognition site, second promoter and a seed infertility polypeptide coding sequence. The at least one activator nucleic acid can encode a transcription activator that binds to the first recognition site, and a different transcription activator that binds to the second recognition site. The promoter for the transcription activator that binds the first recognition site can be a vegetative tissue-specific promoter and the promoter for the transcription activator that binds to the second recognition site can be a seed-specific promoter. The seeds can be dicotyledonous seeds or monocotyledonous seeds.

The invention also features an apomictic plant comprising a first nucleic acid comprising a first transcription activator recognition site and a first promoter, the first recognition site and first promoter operably linked to a sequence to be transcribed, a second nucleic acid comprising a second transcription activator recognition site and a second promoter, the second recognition site and second promoter operably linked to a sequence causing seed infertility. The first and second nucleic acids can be a single nucleic acid molecule. The plant can further contain at least one activator nucleic acid encoding at least one transcription activator that binds to at least one of the recognition sites. Each such transcription activator has a promoter operably linked thereto. The plant can be a dicotyledonous plant or a monocotyledonous plant. The sequence to be transcribed can encode a preselected polypeptide that confers herbicide resistance.

Unless otherwise defined, all technical and scientific terms used herein have the same meaning as commonly understood by one of ordinary skill in the art to which this invention belongs. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description.

BRIEF DESCRIPTION OF TABLES

Tables—Reference Tables

Sequences useful in the instant invention include those described in the Sequence Listing and Reference Tables (sometimes referred to as REF Table).

Reference Tables are found in computer files designated:
Reference_table1__4565.710-0004-55300-US-U-36440.01__1.txt;
Reference_table2__3847.710-0004-55300-US-U-36440.01__1.txt;
Reference_table3__3769.710-0004-55300-US-U-36440.01__1.txt;
Reference_table4__3708.710-0004-55300-US-U-36440.01__1.txt; and
Reference_table5__311987.710-0004-55300-US-U-36440.01__1.txt.

A Reference Table refers to a number of "Maximum Length Sequences" or "MLS." Each MLS corresponds to the longest cDNA and is described in the Av subsection of the Reference Table. The Reference Table includes the following information relating to each MLS:
I. cDNA Sequence
A. 5'UTR
B. Coding Sequence
C. 3'UTR
II. Genomic Sequence
A. Exons
B. Introns
C. Promoters
III. Link of cDNA Sequences to Clone IDs
IV. Multiple Transcription Start Sites
V. Polypeptide Sequences
A. Signal Peptide
B. Domains
C. Related Polypeptides
VI. Related Polynucleotide Sequences
I. cDNA Sequence The Reference Table indicates which sequence in the Sequence Listing represents the sequence of each MLS. The MLS sequence can comprise 5' and 3' UTR as well as coding sequences. In addition, specific cDNA clone numbers also are included in the Reference Table when the MLS sequence relates to a specific cDNA clone.

A. 5'UTR

The location of the 5' UTR can be determined by comparing the most 5' MLS sequence with the corresponding genomic sequence as indicated in the Reference Table. The sequence that matches, beginning at any of the transcriptional start sites and ending at the last nucleotide before any of the translational start sites corresponds to the 5' UTR.

B. Coding Region

The coding region is the sequence in any open reading frame found in the MLS. Coding regions of interest are indicated in the PolyP SEQ subsection of the Reference Table.

C. 3'UTR

The location of the 3' UTR can be determined by comparing the most 3' MLS sequence with the corresponding genomic sequence as indicated in the Reference Table. The sequence that matches, beginning at the translational stop site and ending at the last nucleotide of the MLS corresponds to the 3' UTR.

II. Genomic Sequence

Further, the Reference Table indicates the specific "gi" number of the genomic sequence if the sequence resides in a public databank. For each genomic sequence, Reference tables indicate which regions are included in the MLS. These regions can include the 5' and 3' UTRs as well as the coding sequence of the MLS. See, for example, the scheme below:

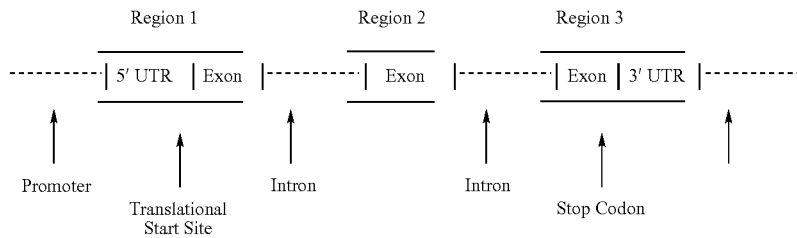

The Reference Table reports the first and last base of each region that are included in an MLS sequence. An example is shown below:
gi No. 47000:
37102 . . . 37497
37593 . . . 37925

The numbers indicate that the MLS contains the following sequences from two regions of gi No. 47000; a first region including bases 37102-37497, and a second region including bases 37593-37925.

A. Exon Sequences

The location of the exons can be determined by comparing the sequence of the regions from the genomic sequences with the corresponding MLS sequence as indicated by the Reference Table.

i. Initial Exon

To determine the location of the initial exon, information from the
(1) polypeptide sequence section;
(2) cDNA polynucleotide section; and
(3) the genomic sequence section
of the Reference Table is used. First, the polypeptide section will indicate where the translational start site is located in the MLS sequence. The MLS sequence can be matched to the genomic sequence that corresponds to the MLS. Based on the match between the MLS and corresponding genomic sequences, the location of the translational start site can be determined in one of the regions of the genomic sequence. The location of this translational start site is the start of the first exon.

Generally, the last base of the exon of the corresponding genomic region, in which the translational start site was located, will represent the end of the initial exon. In some cases, the initial exon will end with a stop codon, when the initial exon is the only exon.

In the case when sequences representing the MLS are in the positive strand of the corresponding genomic sequence, the last base will be a larger number than the first base. When the sequences representing the MLS are in the negative strand of the corresponding genomic sequence, then the last base will be a smaller number than the first base.

ii. Internal Exons

Except for the regions that comprise the 5' and 3' UTRs, initial exon, and terminal exon, the remaining genomic regions that match the MLS sequence are the internal exons. Specifically, the bases defining the boundaries of the remaining regions also define the intron/exon junctions of the internal exons.

iii. Terminal Exon

As with the initial exon, the location of the terminal exon is determined with information from the (1) polypeptide sequence section;
(2) cDNA polynucleotide section; and
(3) the genomic sequence section of the Reference Table. The polypeptide section will indicate where the stop codon is located in the MLS sequence. The MLS sequence can be matched to the corresponding genomic sequence. Based on the match between MLS and corresponding genomic sequences, the location of the stop codon can be determined in one of the regions of the genomic sequence. The location of this stop codon is the end of the terminal exon. Generally, the first base of the exon of the corresponding genomic region that matches the cDNA sequence, in which the stop codon was located, will represent the beginning of the terminal exon. In some cases, the translational start site will represent the start of the terminal exon, which will be the only exon.

In the case when the MLS sequences are in the positive strand of the corresponding genomic sequence, the last base will be a larger number than the first base. When the MLS sequences are in the negative strand of the corresponding genomic sequence, then the last base will be a smaller number than the first base.

B. Intron Sequences

In addition, the introns corresponding to the MLS are defined by identifying the genomic sequence located between the regions where the genomic sequence comprises exons. Thus, introns are defined as starting one base downstream of a genomic region comprising an exon, and end one base upstream from a genomic region comprising an exon.

C. Promoter Sequences

As indicated below, promoter sequences corresponding to the MLS are defined as sequences upstream of the first exon; more usually, as sequences upstream of the first of multiple transcription start sites; even more usually as sequences about 2,000 nucleotides upstream of the first of multiple transcription start sites.

III. Link of cDNA Sequences to Clone IDs

As noted above, the Reference Table identifies the cDNA clone(s) that relate to each MLS. The MLS sequence can be longer than the sequences included in the cDNA clones. In such a case, the Reference Table indicates the region of the MLS that is included in the clone. If either the 5' or 3' termini of the cDNA clone sequence is the same as the MLS sequence, no mention will be made.

IV. Multiple Transcription Start Sites

Initiation of transcription can occur at a number of sites of the gene. The Reference Table indicates the possible multiple transcription sites for each gene. In the Reference Table, the location of the transcription start sites can be either a positive or negative number.

The positions indicated by positive numbers refer to the transcription start sites as located in the MLS sequence. The negative numbers indicate the transcription start site within the genomic sequence that corresponds to the MLS.

To determine the location of the transcription start sites with the negative numbers, the MLS sequence is aligned with the corresponding genomic sequence. In the instances when a public genomic sequence is referenced, the relevant corresponding genomic sequence can be found by direct reference to the nucleotide sequence indicated by the "gi" number shown in the public genomic DNA section of the Reference Table. When the position is a negative number, the transcription start site is located in the corresponding genomic sequence upstream of the base that matches the beginning of the MLS sequence in the alignment. The negative number is relative to the first base of the MLS sequence which matches the genomic sequence corresponding to the relevant "gi" number.

In the instances when no public genomic DNA is referenced, the relevant nucleotide sequence for alignment is the nucleotide sequence associated with the amino acid sequence designated by "gi" number of the later PolyP SEQ subsection.

V. Polypeptide Sequences

The PolyP SEQ subsection lists SEQ ID NOS. and Ceres SEQ ID NO for polypeptide sequences corresponding to the coding sequence of the MLS sequence and the location of the translational start site with the coding sequence of the MLS sequence.

The MLS sequence can have multiple translational start sites and can be capable of producing more than one polypeptide sequence.

Subsection (Dp) provides (where present) information concerning amino acid sequences that are found to be related and have some percentage of sequence identity to the polypeptide sequences of the Reference Tables and Sequence Listing. These related sequences are identified by a "gi" number.

Tables—Protein Group Matrix Tables

In addition to each consensus sequence of the invention, Applicants have generated scoring matrices in Matrix Tables to provide further description of a consensus sequence. The Matrix Tables can be found in computer files:
12514_gly_bra._matrix_table1.txt;
12514._matrix_table2.txt; 12653917._matrix_table3.txt;
23771._matrix_table4.txt; 3000_dico._matrix_table5.txt;
3000._matrix_table6.txt; 1610._matrix_table7.txt;
519._matrix_table8.txt; 8916._matrix_table9.txt;
38419_mono._matrix_table10.txt;
38419._matrix_table11.txt;
38419_dico._matrix_table12.txt;
32791._matrix_table13.txt; 32348._matrix_table14.txt;
5605._matrix_table15.txt;
5605_gly_bra._matrix_table16.txt; and
519gly._matrix_table17.txt. The first row of each matrix indicates the residue position in the consensus sequence. The matrix reports the number of occurrences of all the amino acids that were found in the group members for every residue position of the signature sequence. The matrix also indicates for each residue position, how many different organisms were found to have a polypeptide in the group that included a residue at the relevant position. The last line of the matrix indicates all the amino acids that were found at each position of the consensus. The consensus sequence for each of the above Matrix Tables are in the corresponding Consensus Sequence Table, which contains consensus sequences designated: 12514_gly_bra; 12514; 12653917; 23771; 3000_dico; 3000; 1610; 519; 8916; 38419_mono; 38419; 38419_dico; 32791; 32348; 5605; 5605_gly_bra; and 519_gly.

DETAILED DESCRIPTION

The invention provides novel genetic methods and tools for effectively controlling the transmission of recombinant DNA-based traits from transgenic plants to other cultivars. The invention is based, in part, on the discovery that coordinate expression of certain nucleic acid constructs can control outcrossing and expression of transgenic traits. The method results in the production of infertile seed that carry a gene product for a desired trait. The infertility of the seed prevents unwanted spread of the desired transgenic trait.

Methods for Making Infertile Seed

In one aspect, the invention features a method for making infertile seed. The method comprises permitting seed development to occur on a plurality of first plants that have been pollinated by a plurality of second plants. The first plants can be male-sterile and comprise first and second nucleic acids. The first nucleic acid comprises a first transcription activator recognition site and a first promoter, that are operably linked to a sequence to be transcribed into a desired gene product. The second nucleic acid comprises a second transcription activator recognition site and a second promoter, that are operably linked to a coding sequence causing seed infertility.

The second plants are male-fertile and comprise at least one activator nucleic acid encoding at least one transcription activator and a promoter operably linked thereto. In some embodiments, the transcription activator is effective for binding to both the first and second recognition sites. Upon pollination of the first, male-sterile plants by pollen from the second, male-fertile plants, seed development ensues. The activator nucleic acid carried by the pollen is expressed prior to or during seed development, and the resulting transcription activator activates transcription of the first and the second nucleic acids in developing seeds on the male-sterile female plants. Transcription of the first nucleic acid results in the production of a desired gene product in the resulting seeds, while transcription of the second nucleic acid causes seed infertility. The desired gene product present in the seeds is contained because all, or substantially all, of the seeds are infertile. Thus, unwanted spread of the transgene responsible for the desired trait to the environment, and the desirable trait is effectively contained.

All, or substantially all, of the resulting seeds have a statistically significant increase in the amount of the desired gene product relative to seeds that do not contain or express the first nucleic acid. Seeds made by the method contain the first, the second and the third nucleic acid.

In some embodiments, a single activator nucleic acid encodes two different transcription activators, one of which binds to the first recognition site and the other of which binds to the second recognition site. Alternatively, two different transcription activators can be encoded by separate nucleic acids. In either case, each of the transcription activators can have a different expression pattern, e.g., the transcription activator for the first recognition site can be operably linked to a constitutive promoter and the transcription activator for the second recognition site can be operably linked to a seed-specific promoter. In other embodiments, both transcription activators are operably linked to different, seed-specific promoters.

In some embodiments, the method comprises growing a plurality of plants of an apomictic species. The apomictic plants contain first and second nucleic acids as described above. Typically, the first nucleic acid comprises a first transcription activator recognition site and a first promoter, that are operably linked to a sequence to be transcribed into a desired gene product. The second nucleic acid comprises a second transcription activator recognition site and a second promoter, that are operably linked to a coding sequence causing seed infertility. Such apomictic plants further comprise at least two activator nucleic acids that have different expression patterns. The first activator nucleic acid typically is expressed preferentially in tissues other than seed tissues and floral tissues, whereas the second activator nucleic acid typically is expressed preferentially in seed tissues, e.g., a first transcription activator for the first recognition site is operably linked to a vegetative tissue-specific promoter and a second transcription activator for the second recognition site is operably linked to a seed-specific promoter. In this embodiment, the first transcription activator polypeptide activates transcription of the first nucleic acid, and results in the production of a desired gene product in vegetative tissues, while transcription of the second nucleic acid confers seed infertility. Unwanted spread of the transgene responsible for the desired trait is effectively contained in such apomictic plants.

Desired gene products. Typically, the desired gene product of a sequence to be transcribed is a preselected polypeptide. A preselected polypeptide can be any polypeptide (i.e., 5 or more amino acids joined by a peptide bond). Plants have been used to produce a variety of preselected industrial and pharmaceutical polypeptides, including high value chemicals, modified and specialty oils, enzymes, renewable non-foods such as fuels and plastics, vaccines and antibodies. See e.g., Owen, M. and Pen, J. (eds.), 1996. Transgenic Plants: A Production System for Industrial and Pharmaceutical Proteins. John Wiley & Son Ltd.; Austin, S. et al., 1994. *Annals NY Acad. Sci.* 721:234-242; Austin, S. et al., 1995. *Euphytica* 85: 381-393; Ziegelhoffer, T. et al., 1998. *Molecular Breeding.* U.S. Pat. No. 5,824,779 discloses phytase-protein-pigmenting concentrate derived from green plant juice. U.S. Pat. No. 5,900,525 discloses animal feed compositions containing phytase derived from transgenic alfalfa. U.S. Pat. No. 6,136,320 discloses vaccines produced in transgenic plants. U.S. Pat. No. 6,255,562 discloses insulin. U.S. Pat. No. 5,958,745 discloses the formation of copolymers of 3-hydroxy butyrate and 3-hydroxy valerate. U.S. Pat. No. 5,824,798 discloses starch synthases. U.S. Pat. No. 6,303,341 discloses immunoglobulin receptors. U.S. Pat. No. 6,417,429 discloses immunoglobulin heavy- and light-chain polypeptides. U.S. Pat. No. 6,087,558 discloses the production of proteases in plants. U.S. Pat. No. 6,271,016 discloses an anthranilate synthase gene for tryptophan overproduction in plants.

A preselected polypeptide can be an antibody or antibody fragment. An antibody or antibody fragment includes a humanized or chimeric antibody, a single chain Fv antibody fragment, an Fab fragment, and an F(ab)$_2$ fragment. A chimeric antibody is a molecule in which different portions are derived from different animal species, such as those having a variable region derived from a mouse monoclonal antibody and a human immunoglobulin constant region. Antibody fragments that have a specific binding affinity can be generated by known techniques. Such antibody fragments include, but are not limited to, F(ab')$_2$ fragments that can be produced by pepsin digestion of an antibody molecule, and Fab fragments that can be generated by deducing the disulfide bridges of F(ab')$_2$ fragments. Single chain Fv antibody fragments are formed by linking the heavy and light chain fragments of the Fv region via an amino acid bridge (e.g., 15 to 18 amino acids), resulting in a single chain polypeptide. Single chain Fv antibody fragments can be produced through standard techniques, such as those disclosed in U.S. Pat. No. 4,946,778.

Plant glycans are often non-immunogenic in animals or humans. However, if desired, glycosylation sites can be identified in a preselected polypeptide, and relevant glycosyl transferases can be expressed in parallel with expression of the preselected polypeptide. Alternatively, it may be desirable to prevent glycosylation of a preselected polypeptide, by engineering N-acetylglucosaminyltransferase knock-out plants. If a preselected polypeptide is an antibody or antibody fragment, Asn-X-Ser/Thr sites in the antibody can be deleted.

In some embodiments, the gene product of a sequence to be transcribed is one of the preselected polypeptides in the Table below.

TABLE 1

| | | |
|---|---|---|
| Bromelain | Humatrope ® | Proleukin ® |
| Chymopapain | Humulin ® (insulin) | Protropin ® |
| Papain ® | Infergen ® | Recombivax-HB ® |
| Activase ® | Interferon-gamma-1a | Recormon ® |
| Albutein ® | Interleukin-2 | Remicade ® (s-TNF-r) |
| Angiotensin II | Intron ® | ReoPro ® |
| Asparaginase | Leukine ® (GM-CSF) | Retavase ® (TPA) |
| Avonex ® | Nartogastrim ® | Roferon-A ® |
| Betaseron ® | Neumega ® | Pegaspargas |
| BioTropin ® | Neupogen ® | Prandin ® |
| Cerezyme ® | Norditropin ® | Procrit ® |
| Enbrel ® (s-TNF-r) | Novolin ® (insulin) | Filgastrim ® |
| Engerix-B ® | Nutropin ® | Genotropin ® |
| Epogen ® | Oncaspar ® | Geref ® |
| Sargramostrim | Tripedia ® | Trichosanthin |
| TriHIBit ® | Venoglobin-S ® (HIG) | |

In some embodiments, a sequence to be transcribed results in a desired gene product that is an RNA. Such an RNA, made from a sequence to be transcribed, can be useful for inhibiting expression of an endogenous gene. Suitable DNAs from which such an RNA can be made include an antisense construct and a co-suppression construct. Thus, for example, a sequence to be transcribed can be similar or identical to the sense coding sequence of an endogenous polypeptide, but is transcribed into a mRNA that is unpolyadenylated, lacks a 5' cap structure, or contains an unsplicable intron. Alternatively, a sequence to be transcribed can incorporate a sequence encoding a ribozyme. In another alternative, a sequence to be transcribed can include a sequence that is transcribed into an interfering RNA. Such an RNA can be one that can anneal to itself, e.g., a double stranded RNA having a stem-loop structure. One strand of the stem portion of a double stranded RNA comprises a sequence that is similar or identical to the sense coding sequence of an endogenous polypeptide, and that is from about 10 nucleotides to about 2,500 nucleotides in length. The length of the sequence that is similar or identical to the sense coding sequence can be from 10 nucleotides to 500 nucleotides, from 15 nucleotides to 300 nucleotides, from 20 nucleotides to 100 nucleotides, or from 25 nucleotides to 100 nucleotides. The other strand of the stem portion of a double stranded RNA comprises an antisense sequence of an endogenous polypeptide, and can have a length that is shorter, the same as, or longer than the corresponding length of the sense sequence. The loop portion of a double stranded RNA can be from 10 nucleotides to 5,000 nucleotides, e.g., from 15 nucleotides to 1,000 nucleotides, from 20 nucleotides to 500 nucleotides, or from 25 nucleotides to 200 nucleotides. The loop portion of the RNA can include an intron. See, e.g., WO 99/53050. See, e.g., WO 98/53083; WO 99/32619; WO 98/36083; and WO 99/53050. See also, U.S. Pat. No. 5,034,323. Useful RNA gene products are described in, e.g., U.S. Pat. No. 6,326,527.

In some embodiments, a preselected polypeptide is a polypeptide that confers herbicide resistance on plants expressing the polypeptide. Herbicide resistance is also sometimes referred to as herbicide tolerance. Polypeptides conferring resistance to a herbicide that inhibits the growing point or meristem, such as an imidazolinone or a sulfonylurea can be suitable. Exemplary polypeptides in this category code for mutant ALS and AHAS enzymes as described, for example, in U.S. Pat. Nos. 5,767,366 and 5,928,937. U.S. Pat. Nos. 4,761,373 and 5,013,659 are directed to plants resistant to various imidazolinone or sulfonamide herbicides. U.S. Pat. No. 4,975,374 relates to plant cells and plants containing a gene encoding a mutant glutamine synthetase (GS) resistant to inhibition by herbicides that are known to inhibit GS, e.g. phosphinothricin and methionine sulfoximine. U.S. Pat. No. 5,162,602 discloses plants resistant to inhibition by cyclohexanedione and aryloxyphenoxypropanoic acid herbicides. The resistance is conferred by an altered acetyl coenzyme A carboxylase(ACCase).

Polypeptides for resistance to glyphosate (sold under the trade name Roundup®) are also suitable. See, for example, U.S. Pat. Nos. 4,940,835 and 4,769,061. U.S. Pat. No. 5,554,798 discloses transgenic glyphosate resistant maize plants, in which resistance is conferred by an altered 5-enolpyruvyl-3-phosphoshikimate (EPSP) synthase. Such polypeptides can confer resistance to glyphosate herbicidal compositions, including without limitation glyphosate salts such as the trimethylsulphonium salt, the isopropylamine salt, the sodium salt, the potassium salt and the ammonium salt. See, e.g., U.S. Pat. Nos. 6,451,735 and 6,451,732.

Polypeptides for resistance to phosphono compounds such as glufosinate ammonium or phosphinothricin, and pyridinoxy or phenoxy propionic acids and cyclohexones are also suitable. See European application No. 0 242 246. See also, U.S. Pat. Nos. 5,879,903, 5,276,268 and 5,561,236.

Other herbicides include those that inhibit photosynthesis, such as a triazine and a benzonitrile (nitrilase). See U.S. Pat. No. 4,810,648. Other herbicides include 2,2-dichloropropionic acid, sethoxydim, haloxyfop, imidazolinone herbicides, sulfonylurea herbicides, triazolopyrimidine herbicides, s-triazine herbicides and bromoxynil. Also suitable are herbicides that confer resistance to a protox enzyme. See, e.g., U.S. Patent Application No. 20010016956, and U.S. Pat. No. 6,084,155.

It will be recognized that more than one sequence to be transcribed can be present in some embodiments. For example, coding sequences for two preselected polypeptides may be present on the same or different nucleic acids, and encode polypeptides useful for manipulating a biosynthetic pathway. Alternatively, two coding sequences may be present and encode polypeptides found in a single protein, e.g., a heavy-chain immunoglobulin polypeptide and a light-chain immunoglobulin polypeptide, respectively.

Sequence causing seed infertility. A nucleic acid that results in seed infertility can encode a polypeptide, e.g., a polypeptide involved in seed development, or can form a transcription product. Overexpression or timely expression of such a nucleic acid results in the production of infertile seeds, i.e., seeds that are incapable of producing offspring. In some embodiments, infertile seeds do not germinate. In other embodiments, infertile seeds germinate and form seedlings that do not mature, e.g., seedlings that die before reaching maturity. In yet other embodiments, infertile seeds germinate and form mature plants that are incapable of forming seeds, e.g., that produce no floral structures or abnormal floral structures, or that cannot form gametes.

The product of a nucleic acid that results in seed infertility, i.e., a seed infertility factor, can be an agonist of a polypeptide involved in seed development. Such agonists can be polypeptides (e.g., dominant loss-of-function mutants), and also can be nucleic acids (e.g., antisense nucleic acids, ribozymes, or double-stranded RNA). Those skilled in the art can construct dominant loss of function mutants or nucleic acids using routine methods. Disruption of the function of polypeptides involved in seed development can result in the production of infertile seeds. Polypeptides involved in seed development can be identified, for example, by review of the scientific literature for reports of such polypeptides, by identifying orthologs of polypeptides reportedly involved in seed development, and by genetic screening. Certain nucleic acids suitable for use in conferring seed infertility are described in the Sequence Listing and Reference Tables. See also Table 2 below, which lists clone IDs for some such nucleic acids. Orthologs of these nucleic acids are found in the Ortholog Table in the computer file designated ortholog.txt.

TABLE 2

| Clone ID |
|---|
| clone 32791 |
| clone 332 |
| clone 519 |
| clone 23771 |
| clone 3000 |
| clone 32791 |
| clone 32348 |
| clone 12514 |
| clone 1610 |
| clone 248859 |
| clone 3858 |
| clone 8916 |
| clone 38419 |
| clone 5605 |
| cDNA 1821568 |

An exemplary polypeptide involved in seed development is the FIE polypeptide, which suppresses endosperm development until fertilization occurs. See, U.S. Pat. No. 6,229,064. Seeds that inherit a mutant Fie allele are reported to abort, even if the paternal allele is normal. See, Yadegari, R. et al., Plant Cell 12:2367-81 (2000); U.S. Pat. No. 6,093,874. Other polypeptides for which suppression of expression can cause seed infertility include the products of the DMT and MEA genes. Another exemplary polypeptide involved in seed development is AP2, which is reportedly required for normal seed development. See, U.S. Pat. No. 6,093,874. Two other exemplary polypeptides involved in seed development are INO and ANT, which reportedly are required for ovule integument development. Mutations in INO and ANT reportedly can affect ovule development, resulting in incomplete megasporogenesis. See, WO 00/40694. Thus, transgenes encoding dominant negative suppression polypeptides, or transgenes producing antisense, ribozyme or double stranded RNA gene products can cause seed infertility.

Another exemplary polypeptide involved in seed development is the polypeptide encoded by the LEC2 gene. LEC2 and LEC2-orthologous polypeptides are transcription factors that typically possess a DNA binding domain termed the B3 domain. See, e.g., amino acid residues 165 to 277 in SEQ ID NO:2 of U.S. Pat. No. 6,492,577. A B3 domain can be found in other transcription factors including VIVIPAROUS1, AUXIN RESPONSE FACTOR 1, FUSCA3 and ABI3. Mutations in the LEC2 polypeptide are thought to cause defects in the late seed maturation phase of embryo development.

Another polypeptide involved in seed development is a HAP3-type CCAAT-box binding factor (CBF) subunit. A CBF complex is a heteromeric complex that binds a promoter element having a CCAAT nucleotide sequence motif, often found in the 5' region of eukaryotic genes. CBF complexes bind the CCAAT motif in a wide variety of organisms. CBF complexes include at least two subunits that are involved in binding DNA, as well as one or more subunits that have transcription activation activity. The HAP3-type CBF subunits listed in Table 3 are homologous to the Arabidopsis thaliana HAP3 subunit having GI accession number 3282674. This particular HAP3 type CBF subunit is encoded by the Arabidopsis LEAFY COTYLEDONI (LEC1) gene, which is reportedly required for the specification of cotyledon identity and the completion of embryo maturation. See, e.g., U.S. Pat. Nos. 6,320,102 and 6,235,974. The LEC1 gene reportedly functions at an early developmental stage to maintain embryonic cell fate. LEC1 RNA accumulates during seed development in embryo cell types and in endosperm tissue. Ectopic postembryonic expression of the LEC1 gene in vegetative cells induces the expression of embryo-specific genes and initiates formation of embryo-like structures. Thus LEC1 appears to be an important regulator of embryo development that activates the transcription of genes required for both embryo morphogenesis and cellular differentiation. Also indicative of LEC1's role in seed maturation are the observations that lec1 mutant seed have altered morphology. For example, during seed development the shoot meristem is activated prematurely. Moreover, the embryo does not synthesize seed storage proteins. Finally lec1 seed are desiccation intolerant and die during late embryogenesis. LEC1 CBF subunits can be distinguished from other HAP3-type subunits on the basis of at least one diagnostic conserved sequence. See e.g., WO 99/67405 and WO/00/28058.

TABLE 3

CBF HAP3-TYPE SUBUNITS

| GI Accession Number | Brief Description |
|---|---|
| 3282674 | CCAAT-box binding factor HAP3 homolog [Arabidopsis thaliana] |
| 6552738 | [Arabidopsis thaliana] |
| 9758795 | Contains similarity to CCAAT-box-binding transcription factor~gene__id:MNJ7.26 [Arabidopsis thaliana] |
| 7443520 | Transcription factor, CCAAT-binding, chain A - Arabidopsis thaliana |
| 2398529 | Transcription factor [Arabidopsis thaliana] |
| 9758792 | Contains similarity to CCAAT-box-binding transcription factor~gene__id:MNJ7.23 [Arabidopsis thaliana] |
| 11358889 | Transcription factor NF-Y, CCAAT-binding-like protein - Arabidopsis thaliana |
| 4371295 | Putative CCAAT-box-binding transcription factor [Arabidopsis thaliana] |
| 2398527 | Transcription factor [Arabidopsis thaliana] |
| 115840 | CBFA__MAIZE CCAAT-BINDING TRANSCRIPTION FACTOR SUBUNIT A (CBF-A) |
| 22380 | CAAT-box DNA binding protein subunit B (NF-YB) [Zea mays] |
| 4558662 | Putative CCAAT-box-binding transcription factor [Arabidopsis thaliana] |
| 3928076 | Putative CCAAT-box-binding transcription factor subunit [Arabidopsis thaliana] |
| 203355 | CCAAT binding transcription factor-B subunit [Rattus norvegicus] |
| 104551 | Transcription factor NF-Y, CAAT-binding, chain B - chicken |
| 2133270 | Transcription factor HAP3 - Emericella nidulans |
| 3170225 | Nuclear Y/CCAAT-box binding factor B subunit NF-YB |

TABLE 3-continued

CBF HAP3-TYPE SUBUNITS

| GI Accession Number | Brief Description |
|---|---|
| | [*Xenopus laevis*] |
| 115842 | CBFA_PETMA CCAAT-BINDING TRANSCRIPTION FACTOR SUBUNIT A (CBF-A) |
| 13648093 | Nuclear transcription factor Y, beta [*Homo sapiens*] |
| 3738293 | Putative CCAAT-box-binding transcription factor [*Arabidopsis thaliana*] |
| 115838 | CBFA_CHICK CCAAT-BINDING TRANSCRIPTION FACTOR SUBUNIT A (CBF-A) |
| 115840 | CBFA_MAIZE CCAAT-BINDING TRANSCRIPTION FACTOR SUBUNIT A (CBF-A) |
| 22380 | CAAT-box DNA binding protein subunit B (NF-YB) [*Zea mays*] |
| 4558662 | Putative CCAAT-box-binding transcription factor [*Arabidopsis thaliana*] |
| 3928076 | Putative CCAAT-box-binding transcription factor subunit [*Arabidopsis thaliana*] |
| 203355 | CCAAT binding transcription factor-B subunit [*Rattus norvegicus*] |
| 104551 | Transcription factor NF-Y, CAAT-binding, chain B - chicken |
| 2133270 | Transcription factor HAP3 - *Emericella nidulans* |
| 3170225 | Nuclear Y/CCAAT-box binding factor B subunit NF-YB [*Xenopus laevis*] |
| 115842 | CBFA_PETMA CCAAT-BINDING TRANSCRIPTION FACTOR SUBUNIT A (CBF-A) |
| 13648093 | Nuclear transcription factor Y, beta [*Homo sapiens*] |
| 3738293 | Putative CCAAT-box-binding transcription factor [*Arabidopsis thaliana*] |
| 115838 | CBFA_CHICK CCAAT-BINDING TRANSCRIPTION FACTOR SUBUNIT A (CBF-A) |

Other HAP3-type CBF polypeptides can be identified by homologous nucleotide and polypeptide sequence analyses. Known HAP3-type CBF subunits in one organism can be used to identify homologous subunits in another organism. For example, performing a query on a database of nucleotide or polypeptide sequences can identify homologs of a subunit of a known HAP3-type CBF complex. Homologous sequence analysis can involve BLAST or PSI-BLAST analysis of non-redundant databases using known HAP3-type CBF subunit amino acid sequences. Those proteins in the database that have greater than 40% sequence identity are candidates for further evaluation for suitability as a seed infertility factor polypeptide. If desired, manual inspection of such candidates can be carried out in order to narrow the number of candidates that may be further evaluated. Manual inspection is performed by selecting those candidates that appear to have domains suspected of being present in subunits of HAP3-type CBF complexes.

A percent identity for any subject nucleic acid or amino acid sequence relative to another "target" nucleic acid or amino acid sequence can be determined. For example, conserved regions of polypeptides can be determined by aligning sequences of the same or related polypeptides from closely related plant species. Closely related plant species preferably are from the same family. Alternatively, alignments are performed using sequences from plant species that are all monocots or are all dicots. In some embodiments, alignment of sequences from two different plant species adequate, e.g., sequences from canola and *Arabidopsis* can be used to identify one or more conserved regions.

Typically, polypeptides that exhibit at least about 35% amino acid sequence identity are useful to identify conserved regions in polypeptides. Conserved regions of related proteins sometimes exhibit at least 50% amino acid sequence identity; or at least about 60%; or at least 70%, at least 80%, or at least 90% amino acid sequence identity. In some embodiments, a conserved region of target and template polypeptides exhibit at least 92, 94, 96, 98, or 99% amino acid sequence identity. Amino acid sequence identity can be deduced from amino acid or nucleotide sequence.

Highly conserved domains have been identified within HAP3-type CBF subunits. These conserved regions can be useful in identifying HAP3-type CBF subunits. The primary amino acid sequences of HAP3-type CBF subunits indicate the presence of TATA-box-binding protein association domains as well as histone fold motifs, which are important for protein dimerization. A conserved HAP 3 region derived from this sequence alignment can be represented as follows:

+EQD<2>(L,M)P(I,V)AN(V,I)<1>+IM+<2>aP<2>(A,G)

K(I,V)t(D,K)(D,E)(A,S)K(E,D)<1>aQECVSErISF(I,V)

(T,S)tE(A,L)<1>n+C(Q,H)<1>E(Q,K)RKT(I,V)(T,N)

tnDa<2>Aa<2>LGFn<1>Y<3>L<2>ra<1>+rR, where

| | | | |
|---|---|---|---|
| + | = | "positive" | e.g. H,K,R |
| a | = | "Aliphatic" | e.g. I,L,V,M |
| t | = | "Tiny" | e.g. T,G,A |
| r | = | "Aromatic" | e.g. F,Y,W |
| n | = | "Negative" | e.g. E,D |
| p | = | "Polar" | e.g. N,Q |
| <#> | = | specified # of amino acids, any type | |
| (X,Y) | = | one amino acid, e.g. either X or Y | |

Transcription activators. A transcription activator is a polypeptide that binds to a recognition site on DNA, resulting in an increase in the level of transcription from a promoter operably linked in cis with the recognition site. Many transcription activators have discrete DNA binding and transcription activation domains. The DNA binding domain(s) and transcription activation domain(s) of transcription activators can be synthetic or can be derived from different sources (e.g., two-component system or chimeric transcription activators). In some embodiments, a two-component system transcription activator has a DNA binding domain derived from the yeast gal4 gene and a transcription activation domain derived from the VP16 gene of herpes simplex virus. In other embodiments, a two-component system transcription activator has a DNA binding domain derived from a yeast HAP1 gene and the transcription activation domain derived from VP16. Populations of transgenic organisms or cells having a first nucleic acid construct that encodes a chimeric polypeptide and a second nucleic acid construct that encodes a transcription activator polypeptide can be produced by transformation, transfection, or genetic crossing. See, e.g., WO 97/31064.

Nucleic acid expression. For expression of a sequence to be transcribed, seed infertility factor (polypeptide or nucleic acid agonist), or transcription activator, a coding sequence of the invention is operably linked to a promoter and, optionally, a recognition site for a transcription activator. As used herein, the term "operably linked" refers to positioning of a regulatory element in a nucleic acid relative to a coding sequence so as to allow or facilitate transcription of the coding sequence. For example, a recognition site for a transcription activator is positioned with respect to a promoter so that upon binding of the transcription activator to the recognition site, the level of transcription from the promoter is increased. The position of the recognition site relative to the promoter can be varied for different transcription activators, in order to achieve the desired increase in the level of transcription. Selection and positioning of promoter and transcription activator recognition site is affected by several factors, including, but not limited to, desired expression level, cell or tissue specificity, and inducibility. It is a routine matter for one of skill in the art to modulate the expression of a coding sequence by appropriately selecting and positioning promoters and recognition sites for transcription activators.

A promoter suitable for being operably linked to a transcription activator nucleic acid typically has greater expression in endosperm or embryo, and lower expression in other plant tissues. Such a promoter permits expression of the transcription during seed development, and thus, expression of a sequence to be transcribed during seed development.

A promoter suitable for being operably linked to a sequence to be transcribed can, if desired, have greater expression in one or more tissues of a developing embryo or developing endosperm. For example, such a promoter can have greater expression in the aleurone layer, parts of the endosperm such as chalazal endosperm. Expression typically occurs throughout development. If a sequence to be transcribed is targeted to endosperm and encodes a polypeptide, accumulation of the product can be facilitated by fusing certain amino acid sequences to the amino- or carboxy-terminus of the polypeptide. Such amino acid sequences include KDEL and HDEL, which facilitate targeting of the polypeptide to the endoplasmic reticulum. A histone can be fused to the polypeptide, which facilitates targeting of the polypeptide to the nucleus. Extensin can be fused to the polypeptide, which facilitates targeting to the cell wall. A seed storage protein can be f used to the polypeptide, which facilitates targeting to protein bodies in the endosperm or cotyledons.

Some suitable promoters initiate transcription only, or predominantly, in certain cell types. For example, a promoter specific to a reproductive tissue (e.g., fruit, ovule, seed, pollen, pistils, female gametophyte, egg cell, central cell, nucellus, suspensor, synergid cell, flowers, embryonic tissue, embryo, zygote, endosperm, integument, seed coat or pollen) is used. A cell type or tissue-specific promoter may drive expression of operably linked sequences in tissues other than the target tissue. Thus, as used herein a cell type or tissue-specific promoter is one that drives expression preferentially in the target tissue, but may also lead to some expression in other cell types or tissues as well. Methods for identifying and characterizing promoter regions in plant genomic DNA include, for example, those described in the following references: Jordano, et al., Plant Cell, 1:855-866 (1989); Bustos, et al., Plant Cell, 1:839-854 (1989); Green, et al., EMBO J. 7, 4035-4044 (1988); Meier, et al., Plant Cell, 3, 309-316 (1991); and Zhang, et al., Plant Physiology 110: 1069-1079 (1996).

Exemplary reproductive tissue promoters include those derived from the following seed-genes: zygote and embryo LEC1; suspensor G564; maize MAC1 (see, Sheridan (1996) Genetics 142:1009-1020); maize Cat3, (see, GenBank No. L05934, Abler (1993) Plant Mol. Biol. 22:10131-1038); *Arabidopsis* viviparous-1, (see, Genbank No. U93215); *Arabidopsis* atmycl, (see, Urao (1996) Plant Mol. Biol. 32:571-57, Conceicao (1994) Plant 5:493-505); *Brassica napus* napin gene family, including napA, (see, GenBank No. J02798, Josefsson (1987) JBL 26:12196-1301, Sjodahl (1995) Planta 197:264-271). The ovule-specific promoters FBP7 and DEFH9 are also suitable promoters. Colombo, et al. (1997) Plant Cell 9:703-715; Rotino, et al. (1997) Nat. Biotechnol. 15:1398-1401. The nucellus-specific promoter described in Cehn and Foolad (1997) Plant Mol. Biol. 35:821-831, is also suitable. Early meiosis-specific promoters are also useful. See, Kobayshi et al., (1994) DNA Res. 1:15-26; Ji and Landgridge (1994) Mol. Gen. Genet. 243:17-23. Other meiosis-related promoters include the MMC-specific DMC1 promoter and the SYN1 promoter. See, Klimyuk and Jones (1997) Plant J. 11:1-14; Bai et al. (1999) Plant Cell 11:417-430. Other exemplary reproductive tissue-specific promoters include those derived from the pollen genes described in, for example: Guerrero (1990) Mol. Gen. Genet. 224:161-168; Wakeley (1998) Plant Mol. Biol. 37:187-192; Ficker (1998) Mol. Gen. Genet. 257:132-142; Kulikauskas (1997) Plant Mol. Biol. 34:809-814; and Treacy (1997) Plant Mol. Biol. 34:603-611). Yet other suitable reproductive tissue promoters include those derived from the following embryo genes: *Brassica napus* 2s storage protein (see, Dasgupta (1993) Gene 133:301-302); *Arabidopsis* 2s storage protein; soybean b-conglycinin; *Brassica napus* oleosin 20 kD gene (see, GenBank No. M63985); soybean oleosin A (see, Genbank No. U09118); soybean oleosin B (see, GenBank No. U09119); *Arabidopsis* oleosin (see, GenBank No. Z17657); maize oleosin 18 kD (see, GenBank No. J05212; Lee (1994) Plant Mol. Biol. 26:1981-1987; and the gene encoding low molecular weight sulfur rich protein from soybean, (see, Choi (1995) Mol. Gen, Genet. 246:266-268). Yet other exemplary reproductive tissue promoters include those derived from the following genes: ovule BELL (see Reiser (1995) Cell 83:735-742; Ray (1994) Proc. Natl. Acad. Sci. USA 91:5761-5765; GenBank No. U39944); central cell FIE1; flower primordia *Arabidopsis* APETALA1 (AP1) (see, Gustafson-Brown (1994) Cell 76:131-143; Mandrel (1992) Nature 360:273-277); flower *Arabidopsis* AP2 (see, Drews (1991) Cell 65:991-1002; Bowman (1991) Plant Cell 3:749-758); *Arabidopsis* flower ufo, expressed at the junction between sepal and petal primordia (see, Bossinger (1996) Development 122: 1093-1102); fruit-specific tomato E8; a tomato gene expressed during fruit ripening, senescence and abscission of leaves and flowers (Blume (1997) Plant J. 12:731-746); and pistil-specific potato SK2 (Ficker (1997) Plant Mol. Biol. 35:425-431). See also, WO 98/08961; WO 98/28431; WO 98/36090; U.S. Pat. No. 5,907,082; U.S. Pat. Nos. 6,320,102; 6,235,975; and WO 00/24914. Suitable promoters also include those that are inducible, e.g., by tetracycline (Gatz, 1997), steroids (Aoyama and Chua, 1997), and ethanol (Slater et al. 1998, Caddick et al., 1998).

Nucleic acids. A nucleic acid for use in the invention may be obtained by, for example, DNA synthesis or the polymerase chain reaction (PCR). PCR refers to a procedure or technique in which target nucleic acids are amplified. PCR can be used to amplify specific sequences from DNA as well as RNA, including sequences from total genomic DNA or total cellular RNA. Various PCR methods are described, for example, in PCR Primer: A Laboratory Manual, Dieffenbach, C. & Dveksler, G., Eds., Cold Spring Harbor Laboratory Press, 1995. Generally, sequence information from the ends of the region of interest or beyond is employed to design oligonucleotide primers that are identical or similar in sequence to opposite strands of the template to be amplified. Various PCR strategies are available by which site-specific nucleotide sequence modifications can be introduced into a template nucleic acid.

Nucleic acids for use in the invention may be detected by techniques such as ethidium bromide staining of agarose gels, Southern or Northern blot hybridization, PCR or in situ hybridizations. Hybridization typically involves Southern or Northern blotting. See e.g., Sambrook et al., 1989, Molecular Cloning: A Laboratory Manual, $2^{nd}$ Edition, Cold Spring Harbor Press, Plainview, N.Y., sections 9.37-9.52. Probes should hybridize under high stringency conditions to a nucleic acid or the complement thereof. High stringency conditions can include the use of low ionic strength and high temperature washes, for example 0.015 M NaCl/0.0015 M sodium citrate (0.1×SSC), 0.1% sodium dodecyl sulfate (SDS) at 65° C. In addition, denaturing agents, such as formamide, can be employed during high stringency hybridization, e.g., 50% formamide with 0.1% bovine serum albumin/ 0.1% Ficoll/0.1% polyvinylpyrrolidone/50 mM sodium phosphate buffer at pH 6.5 with 750 mM NaCl, 75 mM sodium citrate at 42° C.

Methods for Making a Polypeptide

In another aspect, the invention features a method for making a polypeptide. The method involves obtaining seed produced as described herein. Such seed are infertile and can be identified by, e.g., the presence of at least the three nucleic acids described above. In some embodiments, there are two transcription activators present in male-fertile plants and, therefore, four nucleic acids, as described above. In some embodiments, a practitioner can obtain seed of the invention by harvesting seeds from both male-sterile and male-fertile plants, or harvesting seeds solely from the male-sterile plants. The choice depends upon, inter alia, whether the two types of parent plants are planted in rows or are randomly interplanted. However, either type of harvesting is encompassed by the invention. In some embodiments, seeds are obtained by purchasing them from a grower. In some embodiments, a practitioner permits male-fertile plants to pollinate male-sterile plants prior to harvesting.

The method also involves extracting the preselected polypeptide, or an endogenous polypeptide, from the seed. Typically, such seeds have a statistically significant increase in the amount of the preselected polypeptide relative to seeds that do not contain or express the first nucleic acid. The choice of techniques to be used for carrying out extraction of a preselected polypeptide will depend on the nature of the polypeptide. For example, if the preselected polypeptide is an antibody, non-denaturing purification techniques may be used. On the other hand, if the preselected polypeptide is a high methionine zein, denaturing techniques may be used. The degree of purification can be adjusted as desired, depending on the nature of the preselected or endogenous polypeptide. For example, an animal feed having an increased amount of an endogenous polypeptide may have no purification, whereas a preselected antibody polypeptide may have extensive purification.

Plants and Seeds

Plants Techniques for introducing exogenous nucleic acids into monocotyledonous and dicotyledonous plants are known in the art, and include, without limitation, *Agrobacterium*-mediated transformation, viral vector-mediated transformation, electroporation and particle gun transformation, e.g., U.S. Pat. Nos. 5,538,880, 5,204,253, 5,591,616, and 6,329,571. If a cell or tissue culture is used as the recipient tissue for transformation, plants can be regenerated from transformed cultures by techniques known to those skilled in the art. Transgenic plants can be entered into a breeding program, e.g., to introduce a nucleic acid into other lines, to transfer a nucleic acid to other species or for further selection of other desirable traits. Alternatively, transgenic plants can be propagated vegetatively for those species amenable to such techniques. Progeny includes descendants of a particular plant or plant line. Progeny of an instant plant include seeds formed on $F_1$, $F_2$, $F_3$, and subsequent generation plants, or seeds formed on $BC_1$, $BC_2$, $BC_3$, and subsequent generation plants. Seeds produced by a transgenic plant can be grown and then selfed (or outcrossed and selfed) to obtain seeds homozygous for the nucleic acid encoding a novel polypeptide.

A suitable group of plants with which to practice the invention include dicots, such as safflower, alfalfa, soybean, rapeseed (high erucic acid and canola), or sunflower. Also suitable are monocots such as corn, wheat, rye, barley, oat, rice, millet, amaranth, sorghum, Kentucky bluegrass, bluestems, weeping lovegrass, or fescues. Also suitable are vegetable crops or root crops such as broccoli, peas, sweet corn, popcorn, tomato, beans (including kidney beans, lima beans, dry beans, green beans) and the like. Also suitable are fruit crops such as peach, pear, apple, cherry, orange, lemon, grapefruit, plum, mango and palm. Thus, the invention has use over a broad range of plants, including species from the genera *Anacardium, Arachis, Asparagus, Atropa, Avena, Bothriochloa, Brassica, Citrus, Citrullus, Capsicum, Carthamus, Cocos, Coffea, Cucumis, Cucurbita, Daucus, Dichanthium, Elaeis, Eragrostis, Fragaria, Glycine, Gossypium, Helianthus, Heterocallis, Hordeum, Hyoscyamus, Lactuca, Linum, Lolium, Lupinus, Lycopersicon, Malus, Manihot, Majorana, Medicago, Nicotiana, Olea, Oryza, Panicum, Pannesetum, Persea, Phaseolus, Pinus, Pistachia, Pisum, Pyrus, Poa, Prunus, Raphanus, Ricinus, Secale, Senecio, Sinapis, Solanum, Sorghum, Theobromus, Trigonella, Triticum, Vicia, Vitis, Vigna* and *Zea*.

Plants of the first type can be male-sterile, e.g., pollen is either not formed or is nonviable. Suitable male-sterility systems are known, including cytoplasmic male sterility (CMS), nuclear male sterility, genetic male sterility, and molecular male sterility wherein a transgene inhibits microsporogenesis and/or pollen formation. Female parent plants containing CMS are particularly useful. In the case of *Brassica* species, CMS can be, for example of the ogu, nap, pol, mur, or tour type. See, e.g., U.S. Pat. Nos. 6,399,856, 6,262,341; 6,262,334; 6,392,119 and 6,255,564. In the case of corn, a number of different methods of conferring male sterility are available, such as multiple mutant genes at separate locations within the genome that confer male sterility. In addition, one can use transgenes to silence one or more nucleic acid sequences necessary for male fertility. See, U.S. Pat. Nos. 4,654,465, 4,727,219, and 5,432,068. See also, EPO publication no. 329, 308 and PCT application WO 90/08828.

Alternatively, plants of both the first type and the second type can be male-fertile. In this case, plants of the first type can be pollinated by hand, using pollen from plants of the second type. In some embodiments, pollen-forming structures on plants of the first type are removed in order to prevent self-pollination of first plants, thereby permitting manual or natural pollination by pollen from second plants. One can also use gametocides to inhibit or prevent pollen formation on plants of the first type. Gametocides are chemicals that affect cells critical to male fertility. Typically, a gametocide affects fertility only in the plants to which the gametocide is applied. Application of the gametocide, timing of the application and genotype can affect the usefulness of the approach. See, U.S. Pat. No. 4,936,904. In some embodiments, plants are of a species that exhibits partial or complete self-incompatibility, e.g., alfalfa, *Brassica rapa*, or potato. When complete self-incompatibility is present, measures such as male sterility systems or removal of pollen-forming structures on plants of the first type may not be necessary.

Articles of Manufacture

A plant seed composition of the invention can contain seeds of the first type of plant and of the second type of plant.

Seeds of the first type of plant typically are of a single variety, as are seeds of the second type of plant.

The proportion of seeds of each type of plant in a composition is measured as the number of seeds of a particular type divided by the total number of seeds in the composition, and can be formulated as desired to meet requirements based on geographic location, pollen quantity, pollen dispersal range, plant maturity, choice of herbicide, and the like. The proportion of the first variety can be from about 70 percent to about 99.9 percent, e.g., 90%, 91%, 92%, 93%, 94%, 95%, 96%, 97%, 98%, or 99%. The proportion of the second type can be from about 0.1 percent to about 30 percent, e.g., 0.5%, 1%, 2%, 5%, 10%, 15%, or 30%. When large quantities of a seed composition are formulated, or when the same composition is formulated repeatedly, there may be some variation in the proportion of each type observed in a sample of the composition, due to sampling error. In the present invention, such sampling error typically is about ±5% of the expected proportion, e.g., 90%±4.5%, or 5%±0.25%.

For example, a seed composition of the invention can be made from two corn varieties. A first corn variety can constitute 92% of the seeds in the composition and be male-sterile, and carry a first nucleic acid encoding one or more polypeptides involved in the synthesis of poly(3-hydroxybutyrate-co-3-hydroxyvalerate. A second corn variety can constitute 8% of the seed in the composition and be male-fertile, and carry a third nucleic acid encoding a transcription activator that recognizes a transcription recognition site operably linked to a nucleic acid encoding a preselected polypeptide. Thus, such a seed composition can be used to grow plants that are suitable for practicing a method of the invention.

Typically, a substantially uniform mixture of seeds of each of the types is conditioned and bagged in packaging material by means known in the art to form an article of manufacture. Such a bag of seed preferably has a package label accompanying the bag, e.g., a tag or label secured to the packaging material, a label printed on the packaging material or a label inserted within the bag. The package label indicates that the seeds therein are a mixture of varieties, e.g., two different varieties. The package label may indicate that plants grown from such seeds are suitable for making an indicated preselected polypeptide. The package label also may indicate the seed mixture contained therein incorporate transgenes that provide biological containment of the transgene encoding the preselected polypeptide.

Plants grown from the varieties in a seed composition of the invention typically have the same or very similar maturity, i.e., the same or very similar number of days from germination to crop seed maturation. In some embodiments, however, one or more varieties in a seed composition of the invention can have a different relative maturity compared to other varieties in the composition. For example, the first type of plants grown from a seed composition can be classified as having a 105 day relative maturity, while the second type of plants grown from the seed composition can be classified as having a 110 day relative maturity. The presence of plants of different relative maturities in a seed composition can be useful as desired to properly coordinate optimum pollen receptivity of the first type of plants with optimum pollen shed from the second type of plants. Relative maturity of a variety of a given crop species is classified by techniques known in the art.

In some embodiments, a plant seed composition of the invention comprises seeds of an apomictic plant species. Seeds of an apomictic species in such a composition constitute at least about 90% of the seeds in the composition, e.g., at least 91%, 93%, 95%, 97% or 99%. Typically the apomictic seeds are of a single variety. Apomictic plant species include facultative apomicts such as weeping lovegrass, Kentucky bluegrass, or bluestems, as well as obligate apomicts. Apomictic mechanisms in seeds of the composition can be classified as aposporous or diplosporous, primarily in grasses, or adventitious embryony, found in citrus. Seeds of an apomictic plant species in such a composition contain nucleic acid constructs as discussed herein, and can be germinated and grown to form plants whose seeds are infertile. The infertility of the seed prevents unwanted spread of a desired transgenic trait present in such plants to other plants of the same species.

The invention is further described in the following examples, which do not limit the scope of the invention described in the claims.

EXAMPLES

Example 1

Chimeric LEC2 Nucleic Acid Construct

A chimeric LEC2 gene construct, designated pLEC2, was made using standard molecular biology techniques. The construct contains the coding sequence for the *Arabidopsis* LEC2 polypeptide. pLEC2 contains 5 binding sites for the DNA binding domain upstream activation sequence of the Hap1 transcription factor ($UAS_{Hap1}$) located 5' to and operably linked to a CaMV35S minimal promoter. The CaMV35S minimal promoter is located 5' to and operably linked to the LEC2 coding sequence. The construct contains an OCS polyA transcription terminator sequence operably linked to the 3' end of the LEC2 coding sequence. The binding of a transcription factor that possesses a Hap 1 DNA binding domain to the $UAS_{Hap1}$ is necessary for transcriptional activation of the LEC2 chimeric gene.

Example 2

Transgenic Rice Plants

The pLEC2 plasmid was introduced into the Japonica rice cultivar Kitaake by *Agrobacterium tumefaciens* mediated transformation using techniques similar to those described in U.S. Pat. No. 6,329,571. Transformants were selected based on resistance to the herbicide bialophos, conferred by a bar gene present on the introduced nucleic acid. After selfing to homozygosity for 3 generations, several transformed plants, designated pLEC2-3-11-10, pLEC2-3-11-12, pLEC2-3-11-13, pLEC2-3-12-2, pLEC2-3-12-4, were selected for further study.

A construct designated pCR19, containing a chimeric Hap1-VP16 gene and a green fluorescent protein (GFP) reporter gene was introduced into the Kitaake cultivar by the same technique. The chimeric Hap1-VP16 gene contained a rice ubiquitin minimal promoter operably linked to the 5' end of the Hap 1-VP16 coding sequence and an NOS polyA terminator operably linked to the 3' end of the Hap1-VP16 coding sequence. The amino acid sequence of the HAP1 portion of the Hap 1-VP16 transcription activator is that of the yeast Hap1 gene. The GFP reporter gene included 5 copies of a $UAS_{HAP1}$ upstream activator sequence element operably linked 5' to the GFP coding sequence and an OCS polyA terminator operably linked 3' to the GFP coding sequence.

Transformants were selected based on bialophos resistance conferred by a bar gene, and then screened for plants in which expression of GFP was targeted to the embryo. After selfing for 2 generations and verifying embryo-specific expression of the Hap1-VP16 coding sequence, 2 heterozygous transformed plants, designated CR19-60-1 and CR19-60-2, were selected for further study. By microscopic evaluation, these plants showed high levels of GFP expression in developing embryos, little or no GFP expression in endosperm, and low levels of GFP expression in seedlings.

Rice plants homozygous for the LEC2 transgene were crossed as females with CR19-60-1 and CR19-60-2 plants. Samples of the developing $F_1$ embryos were collected at 5 days, 8 days, and 12 days after pollination.

Nine embryos collected at 5 days after pollination were observed under a dissecting microscope and a fluorescent microscope. The presence or absence of the Hap1-VP16 chimeric gene was determined based on the presence or absence of GFP reporter gene activity as visualized with a UV-equipped microscope. Four embryos were found to have received the Hap1-VP16 gene. The development of these embryos was delayed and was equivalent to the development of a corresponding control embryo at 3 days after pollination. In addition, the scutellum and first leaf were found to be fused. The other 5 embryos did not have the Hap1-VP16 chimeric gene and showed normal development.

At 8 days after pollination, developing embryos were placed on phytohormone-free MS germination media and germination was observed for up to 24 days. Of 10 embryos evaluated, 1 embryo contained both Hap1-VP16 and LEC2. This embryo was found to have lost the ability to germinate. The other 9 control embryos did not contain the Hap1-VP16 chimeric gene, and formed normal seedlings.

Seventeen embryos collected at 12 days after pollination were dissected by cutting longitudinally through the embryonic axis. Dissected embryos were then observed under a dissecting microscope, and it was found that the 7 Hap1-VP16 expressing embryos formed multiple shoots but no root primordium initiation. In addition, the leaves were not well developed. The other 10 embryos did not contain Hap1-VP16 and showed normal shoot, root and leaf differentiation.

Mature $F_1$ seed was collected 27 days after pollination and allowed to dry. Thirteen seeds contained both pLEC2 and the activation construct CR19. Twenty five seeds contained the pLEC2 construct only. $F_1$ seeds, together with control seeds, were germinated on agar plates containing hormone-free 0.5× Murashige and Skoog (MS) salts, 1.5 percent sucrose and 0.25 percent Gelrite. Germination efficiency was scored 19 days later. Seeds containing Hap1-VP16 and expressing LEC2 were completely infertile and had 0% germination, whereas control seeds had 100% germination. These data indicate that embryo-targeted LEC2 expression results in infertile seed.

A similar experiment was conducted using Hap1-VP16 lines selected for targeting to the endosperm. Two different endosperm-specific promoters were used to drive Hap1-VP16. Transgenic plants obtained from each transformation expressed GFP targeted to endosperm only. Plants homozygous for Hap1-VP16 and GFP were obtained after selfing for 2 generations and used to pollinate the pLEC2 homozygous plants. Mature $F_1$ seed was collected and allowed to dry. F1 Seeds containing Hap1-VP16 and expressing LEC2 were fertile and had a normal germination rate on the phytohormone-free MS medium. These data indicate that endosperm-targeted LEC2 expression results in fertile seed.

Example 3

Transgenic Soybean Plants

A soybean plant homozygous for a transgene comprising the LEC2 coding sequence operably linked to 5 copies of a $UAS_{Hap1}$ and a 35S minimal promoter is crossed as a female, using pollen from a soybean plant homozygous for a transgene comprising a HAP1-VP16 polypeptide operably linked to an embryo-targeted regulatory sequence. The soybean plant used as a female also is homozygous for a transgene comprising the coding sequence for a tumor necrosis factor receptor polypeptide, operably linked to 5 copies of a $UAS_{Hap1}$ and a 35S minimal promoter. See, e.g., U.S. Pat. No. 6,541,610.

At maturity, $F_1$ seeds are collected and stored under standard conditions. Any tumor necrosis factor receptor expressed in the $F_1$ seeds is extracted. At 7, 14, and 21 days after pollination, some of the embryos and seeds developing on $F_1$ plants are examined under a microscope. Mature seed also are scored for viability and germination and tested for the presence of tumor necrosis factor receptor coding sequence by PCR. The procedure is repeated using corn plants instead of soybean plants.

It is to be understood that while the invention has been described in conjunction with the detailed description thereof, the foregoing description is intended to illustrate and not limit the scope of the invention.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07476777B2). An electronic copy of the "Sequence Listing" will also be available from the USPTO upon request and payment of the fee set forth in 37 CFR 1.19(b)(3).

What is claimed is:

1. A method for making infertile seed, said method comprising:
   a) growing a plurality of apomictic plants, wherein said plants comprise first and second nucleic acids, said first nucleic acid comprising a first transcription activator recognition site and a first promoter, said first recognition site and said first promoter operably linked to a sequence to be transcribed, said second nucleic acid comprising a second transcription activator recognition site and a second promoter, said second recognition site and said second promoter operably linked to a coding sequence that results in seed infertility, wherein said coding sequence that results in seed infertility is SEQ ID NO: 70; and wherein said plants comprise at least one activator nucleic acid comprising at least one coding sequence for a transcription activator that binds to at least one of said recognition sites, each said at least one transcription activator coding sequence having a promoter operably linked thereto, and wherein seeds that form on said plants are infertile, wherein said first and second promoters and said promoter operably linked to said at least one transcription activator coding sequence are selected from a CaMV35S minimal promoter and a rice or maize ubiquitin minimal promoter; wherein said first and second transcription activator recognition sites comprise from 1 to 5 copies of a $UAS_{Hap1}$ upstream activator sequence element; and wherein said transcription activator is a chimeric polypeptide comprising a yeast HAP1 DNA binding domain and a herpes simplex VP16 transcription activator domain.

2. The method of claim 1, wherein said plants are dicotyledonous plants.

3. The method of claim 1, wherein said plants are monocotyledonous plants.

4. The method of claim 1, wherein said sequence to be transcribed encodes a preselected polypeptide.

5. The method of claim 4, wherein expression of said preselected polypeptide confers herbicide resistance.

6. A method for making a polypeptide, said method comprising:
   a) growing a plurality of apomictic plants, each of said plants comprising: i) a first nucleic acid comprising a first transcription activator recognition site and a first promoter, said first recognition site and said first promoter operably linked to a nucleic acid encoding a preselected polypeptide; and ii) a second nucleic acid comprising a second transcription activator recognition site and a second promoter, said second recognition site and said second promoter operably linked to a sequence causing seed infertility, wherein said sequence causing seed infertility is SEQ ID NO: 70 and wherein said plants comprise at least one activator nucleic acid encoding at least one transcription activator that binds to at least one of said recognition sites, each said at least one transcription activator nucleic acid having a promoter operably linked thereto, wherein said first and second promoters and said promoter operably linked to said at least one transcription activator nucleic acid are selected from a CaMV35S minimal promoter and a rice or maize ubiquitin minimal promoters; wherein said first and second transcription activator recognition sites comprise from 1 to 5 copies of a $UAS_{Hap1}$ upstream activator sequence element; and wherein said transcription activator is a chimeric polypeptide comprising a yeast HAP1 DNA binding domain and a herpes simplex VP16 transcription activator domain; and
   b) expressing said preselected polypeptide in said plants, wherein said plants have a statistically significant increase in said preselected polypeptide relative to plants that do not contain or express said first nucleic acid and wherein seeds that develop on said plants are infertile.

7. An article of manufacture comprising:
   a) a container;
   b) apomictic seeds within said container, said seeds comprising at least one first nucleic acid comprising: i) a first transcription activator recognition site and a first promoter, said first recognition site and said first promoter operably linked to a sequence to be transcribed; ii) a second transcription activator recognition site and a second promoter, said second recognition site and said second promoter operably linked to a sequence causing seed infertility wherein said sequence causing seed infertility is SEQ ID NO: 70; and iii) at least one activator nucleic acid encoding at least one transcription activator that binds to at least one of said recognition sites, each said at least one transcription activator nucleic acid having a promoter operably linked thereto, wherein plants grown from said seeds are infertile, wherein said first and second promoters and said promoter operably linked to said at least one transcription activator nucleic acid are selected from a CaMV35S minimal promoter and a rice or maize ubiquitin minimal promoter; wherein said first and second transcription activator recognition sites comprise from 1 to 5 copies of a $UAS_{Hap1}$ upstream activator sequence element; and wherein said transcription activator is a chimeric polypeptide comprising a yeast HAP1 DNA binding domain and a herpes simplex VP16 transcription activator domain.

8. The method of claim 7, wherein said sequence to be transcribed encodes a preselected polypeptide.

9. The article of claim 7, wherein said seeds are dicotyledonous seeds.

10. The article of claim 7, wherein said seeds are monocotyledonous seeds.

11. An apomictic plant comprising:
   a) a first nucleic acid comprising a first transcription activator recognition site and a first promoter, said first recognition site and said first promoter operably linked to a sequence to be transcribed,
   b) a second nucleic acid comprising a second transcription activator recognition site and a second promoter, said second recognition site and said second promoter operably linked to a sequence causing seed infertility, wherein said sequence causing seed infertility is SEQ ID NO:70, and
   c) at least one activator nucleic acid comprising at least one coding sequence for a transcription activator that binds to at least one of said recognition sites, each said at least one transcription activator coding sequence having a promoter operably linked thereto,
   wherein seeds that develop on said plant are infertile, wherein said first and second promoters and said promoter operably linked to said at least one transcription activator coding sequence are selected from a CaMV35S minimal promoter and a rice or maize ubiquitin minimal promoter; wherein said first and second transcription activator recognition sites comprise from 1 to 5 copies of a $UAS_{Hap1}$ upstream activator sequence element; and wherein said transcription activator is a chimeric polypeptide comprising a yeast HAP1 DNA binding domain and a herpes simplex VP16 transcription activator domain.

12. The plant of claim 11, wherein said plant is a dicotyledonous plant.

13. The plant of claim 11, wherein said plant is a monocotyledonous plant.

14. The plant of claim 11, wherein said sequence to be transcribed encodes a preselected polypeptide that confers herbicide resistance.

* * * * *

UNITED STATES PATENT AND TRADEMARK OFFICE
CERTIFICATE OF CORRECTION

PATENT NO. : 7,476,777 B2
APPLICATION NO. : 10/873679
DATED : January 13, 2009
INVENTOR(S) : Peter N. Mascia Page 1 of 1

It is certified that error appears in the above-identified patent and that said Letters Patent is hereby corrected as shown below:

Column 27, line 61 (Claim 6), please delete "promoters" and insert --promoter-- therefor;

Column 28, line 36 (Claim 8), please delete "method" and insert --article-- therefor;

Column 28, line 37 (Claim 8), please delete "encodes" and insert --is-- therefor.

Signed and Sealed this

Sixteenth Day of June, 2009

JOHN DOLL
*Acting Director of the United States Patent and Trademark Office*